(12) United States Patent
Saadat

(10) Patent No.: US 11,154,696 B2
(45) Date of Patent: *Oct. 26, 2021

(54) SURGICAL DEVICE WITH INTEGRATED VISUALIZATION AND CAUTERIZATION

(71) Applicant: Arrinex, Inc., Menlo Park, CA (US)

(72) Inventor: Vahid Saadat, Atherton, CA (US)

(73) Assignee: Arrinex, Inc., Redwood City, CA (US)

( * ) Notice: Subject to any disclaimer, the term of this patent is extended or adjusted under 35 U.S.C. 154(b) by 137 days.

This patent is subject to a terminal disclaimer.

(21) Appl. No.: 16/222,847

(22) Filed: Dec. 17, 2018

(65) Prior Publication Data

US 2019/0381290 A1     Dec. 19, 2019

Related U.S. Application Data

(63) Continuation of application No. 14/957,475, filed on Dec. 2, 2015, now Pat. No. 10,201,687, which is a
(Continued)

(51) Int. Cl.
*A61M 29/00*     (2006.01)
*A61B 17/32*     (2006.01)
(Continued)

(52) U.S. Cl.
CPC ......... *A61M 29/00* (2013.01); *A61B 1/00087* (2013.01); *A61B 1/00089* (2013.01);
(Continued)

(58) Field of Classification Search
CPC .............. A61B 17/0218; A61B 17/295; A61B 17/3201; A61B 17/3203; A61B 17/32002;
(Continued)

(56) References Cited

U.S. PATENT DOCUMENTS 5,353,784 A   10/1994  Nady-Mohamed
5,527,351 A    6/1996  Friedman et al.
(Continued)

FOREIGN PATENT DOCUMENTS

EP    2532300 A2   12/2012
EP    2662027 A1   11/2013
(Continued)

OTHER PUBLICATIONS

Arora, et al., "Cryodestruction of Vidian Nerve Branches", Indian Journal of Otolaryngology, vol. 31, No. 3, Sep. 1980, pp. 80-82.
(Continued)

*Primary Examiner* — Kathleen S Holwerda
*Assistant Examiner* — Kankindi Rwego
(74) *Attorney, Agent, or Firm* — McDonnell Boehnen Hulbert & Beghoff LLP

(57) ABSTRACT

Surgical devices with integrated visualization and cauterization are described herein where such devices include an elongate structure having a central lumen and an expandable space-creating structure having at least one expandable leaflet mounted in the vicinity of the distal end and is configured for placement within a mammalian body proximate to a therapeutic target. Also included is a proximal terminal having an actuator mounted in the vicinity of the proximal end and is configured to remain outside of said body and provide an actuation mechanism for actuating the space-creating structure. Additionally, at least one fluid connector and said central lumen is in fluid communication between an interior of the expandable space-creating structure and the at least one fluid connector.

20 Claims, 24 Drawing Sheets

Related U.S. Application Data continuation of application No. 14/168,717, filed on Jan. 30, 2014, now abandoned.

(60) Provisional application No. 61/762,660, filed on Feb. 8, 2013.

(51) Int. Cl.
| | | |
|---|---|---|
| *A61B 17/3203* | (2006.01) | |
| *A61B 1/00* | (2006.01) | |
| *A61B 1/05* | (2006.01) | |
| *A61B 17/02* | (2006.01) | |

(52) U.S. Cl.
CPC ...... *A61B 1/00135* (2013.01); *A61B 1/00183* (2013.01); *A61B 1/05* (2013.01); *A61B 17/0218* (2013.01); *A61B 17/32002* (2013.01); *A61B 17/3203* (2013.01); *A61B 2017/320024* (2013.01)

(58) Field of Classification Search
CPC .. A61B 17/320016; A61B 2017/32004; A61B 1/00096; A61B 1/00177; A61B 1/00174; A61B 1/00179; A61B 1/00181; A61B 1/00183; A61B 1/00094; A61B 2017/22079; A61B 2017/32007; A61B 2017/32008; A61B 2217/005; A61B 2217/007; A61B 17/29; A61B 2017/2926; A61B 2017/2945; A61B 10/0283; A61B 10/06; A61M 1/0084; A61M 29/00; A61M 29/02; A61M 2029/025
USPC .......................................................... 606/192
See application file for complete search history.

(56) References Cited

U.S. PATENT DOCUMENTS

| | | | |
|---|---|---|---|
| 5,611,796 A | 3/1997 | Kamami | |
| 5,658,307 A * | 8/1997 | Exconde | A61B 17/00234 606/190 |
| 5,733,280 A | 3/1998 | Avitall | |
| 5,827,305 A * | 10/1998 | Gordon | A61F 9/00763 606/159 |
| 5,899,898 A | 5/1999 | Arless et al. | |
| 5,899,899 A | 5/1999 | Arless et al. | |
| 6,106,518 A | 8/2000 | Wittenberger et al. | |
| 6,139,508 A * | 10/2000 | Simpson | A61B 10/06 600/564 |
| 6,210,035 B1 | 4/2001 | Edwards et al. | |
| 6,270,476 B1 | 8/2001 | Santoianni et al. | |
| 6,595,988 B2 | 7/2003 | Wittenberger et al. | |
| 7,104,984 B2 | 9/2006 | Ryba et al. | |
| 7,300,433 B2 | 11/2007 | Lane et al. | |
| 7,418,292 B2 | 8/2008 | Shafer et al. | |
| 7,527,601 B2 | 5/2009 | Dubey | |
| 7,769,442 B2 | 8/2010 | Shafer et al. | |
| 8,088,127 B2 | 1/2012 | Mayse et al. | |
| 8,142,424 B2 | 3/2012 | Swanson et al. | |
| 8,231,613 B2 | 7/2012 | Baxter et al. | |
| 8,382,746 B2 | 2/2013 | Williams et al. | |
| 8,388,600 B1 | 3/2013 | Elderedge et al. | |
| 8,394,075 B2 | 3/2013 | Ansarinia et al. | |
| 8,425,457 B2 | 4/2013 | Chang et al. | |
| 8,512,324 B2 | 8/2013 | Abboud et al. | |
| 8,676,324 B2 | 3/2014 | Simon et al. | |
| 8,679,104 B2 | 3/2014 | Abboud et al. | |
| 8,715,275 B2 | 5/2014 | Burger et al. | |
| 8,996,137 B2 | 5/2015 | Wardle et al. | |
| 9,050,073 B2 | 6/2015 | Newell et al. | |
| 9,084,592 B2 | 7/2015 | Wu et al. | |
| 9,168,081 B2 | 10/2015 | Williams et al. | |
| 9,265,956 B2 | 2/2016 | Ackermann et al. | |
| 10,201,687 B2 * | 2/2019 | Saadat | A61B 17/32002 |
| 2002/0029006 A1 * | 3/2002 | Turturro | A61B 10/06 600/562 |
| 2003/0114659 A1 | 7/2003 | Edwards et al. | |
| 2004/0224412 A1 | 2/2004 | Clements et al. | |
| 2005/0096502 A1 | 5/2005 | Khalili | |
| 2006/0235474 A1 | 10/2006 | Demarais et al. | |
| 2006/0276852 A1 | 12/2006 | Demarais et al. | |
| 2007/0173899 A1 | 7/2007 | Levin et al. | |
| 2007/0265687 A1 | 11/2007 | Deem et al. | |
| 2007/0299433 A1 | 12/2007 | Williams et al. | |
| 2008/0027423 A1 | 1/2008 | Choi et al. | |
| 2008/0119693 A1 | 5/2008 | Makower et al. | |
| 2008/0208230 A1 * | 8/2008 | Chin | A61B 17/32002 606/167 |
| 2009/0030276 A1 | 1/2009 | Saadat | |
| 2009/0036948 A1 | 2/2009 | Levin et al. | |
| 2009/0062873 A1 | 3/2009 | Wu et al. | |
| 2009/0076409 A1 | 3/2009 | Wu et al. | |
| 2009/0187074 A1 | 7/2009 | Saadat | |
| 2009/0234345 A1 | 9/2009 | Hon et al. | |
| 2009/0326572 A1 | 12/2009 | Peh | |
| 2010/0057150 A1 | 3/2010 | Demarais et al. | |
| 2010/0137860 A1 | 6/2010 | Demarais et al. | |
| 2010/0137952 A1 | 6/2010 | Demarais et al. | |
| 2010/0168731 A1 | 7/2010 | Wu et al. | |
| 2010/0168739 A1 | 7/2010 | Wu et al. | |
| 2010/0174282 A1 | 7/2010 | Demarais et al. | |
| 2010/0191112 A1 | 7/2010 | Demarais et al. | |
| 2010/0256629 A1 | 10/2010 | Wylie | |
| 2011/0152855 A1 | 6/2011 | Mayse et al. | |
| 2011/0184402 A1 | 7/2011 | Baust et al. | |
| 2012/0016260 A1 * | 1/2012 | To | A61B 17/3417 600/562 |
| 2013/0006326 A1 | 1/2013 | Ackermann et al. | |
| 2013/0018366 A1 | 1/2013 | Wu et al. | |
| 2013/0253387 A1 | 9/2013 | Bonutti et al. | |
| 2013/0310822 A1 | 11/2013 | Mayse et al. | |
| 2013/0345700 A1 | 12/2013 | Hlavka et al. | |
| 2014/0186341 A1 | 7/2014 | Mayse et al. | |
| 2014/0236148 A1 | 8/2014 | Hlavka et al. | |
| 2014/0257271 A1 | 9/2014 | Mayse et al. | |
| 2014/0276792 A1 | 9/2014 | Kaveckis et al. | |
| 2014/0277429 A1 | 9/2014 | Kuzma et al. | |
| 2014/0316310 A1 | 10/2014 | Ackermann et al. | |
| 2014/0371812 A1 | 12/2014 | Ackermann et al. | |
| 2015/0031946 A1 | 1/2015 | Saadat et al. | |
| 2015/0080870 A1 | 3/2015 | Wittenberger | |
| 2015/0126986 A1 | 5/2015 | Kelly et al. | |
| 2015/0164571 A1 | 6/2015 | Saadat | |
| 2015/0196345 A1 | 7/2015 | Newell et al. | |
| 2015/0238754 A1 | 8/2015 | Loudin et al. | |
| 2015/0313661 A1 | 11/2015 | Wu et al. | |
| 2016/0022992 A1 | 1/2016 | Franke et al. | |
| 2016/0045277 A1 | 2/2016 | Lin et al. | |
| 2016/0101286 A1 | 4/2016 | Franke et al. | |
| 2016/0114163 A1 | 4/2016 | Loudin et al. | |
| 2016/0114172 A1 | 4/2016 | Loudin et al. | |
| 2016/0158548 A1 | 6/2016 | Ackermann et al. | |

FOREIGN PATENT DOCUMENTS

| | | |
|---|---|---|
| EP | 2662116 A1 | 11/2013 |
| EP | 2862046 B1 | 5/2019 |
| WO | 2008051918 A2 | 5/2008 |
| WO | 2012027641 A3 | 5/2012 |
| WO | 2013035192 A1 | 3/2013 |
| WO | 2013173481 A2 | 11/2013 |

OTHER PUBLICATIONS

Bumsted, "Cryotherapy for Chronic Vasomotor Rhinitis: Technique and Patient Selection or Improved Results", Laryngoscope, vol. 94, Apr. 1984, pp. 539-544.

Girdar-Gopal, An Assessment of Postganglionic Cryoneurolysis for Managing Vasomotor Rhinitis:, American Journal of Rhinology, vol. 8, No. 4, Jul.-Aug. 1994, pp. 157-164.

(56) References Cited

OTHER PUBLICATIONS

Golhar, et al., "The effect of Cyrodestruction of Vidian Nasal Branches on Nasal Mucus Flow in Vasomotor Rhinitis", Indian Journal of otolaryngology, vol. 33, No. 1, Mar. 1981, pp. 12-14.
Goode, "A Liquid Nitrogen Turbinate Probe for Hypertrophic Rhinitis", Arch Otolaryngol., vol. 103, 1977, p. 431.
Mehra, et al., "Cryosurgery in Vasomotor Rhinitis—An Analysis of 156 Patients", Indian Journal of Otolaryngology, vol. 83, No. 4, 1973, pp. 508-516.
Ozenberger, "Cryosurgery for the Treatment of Chronic Rhinitis", Laryngoscope, vol. 83, No. 4, 1973, pp. 508-516.
Ozenberger, "Cryosurgery in Chronic Rhinitis", The Laryngoscope, vol. 80, No. 5, May 1970, pp. 723-734.
Principato, "Chronic Vasomotor Rhinitis: Cryogenic and Other Surgical Modes of Treatment", The Laryngoscope, vol. 89, 1979, pp. 619-638.
Rao, "Cryosurgery on Inferior turbinate hypertrophy under topical anaesthesia—is it boon in electricity deprived places", National Journal of otorhinolaryngology and Head & Neck Surgery, vol. 1 {10}, No. 1, Apr. 2013, pp. 7-9.
Strome, "A long-term assessment of cryotherapy for treating vasomotor instability", vol. 69, No. 12, http://apps.webofknowledge.com.laneproxy.standford.edu/OutboundService . . . marked_list_candidates=1&excludeEventConfig=ExcludelfFromFuiiRecPage, Dec. 1990, pp. 839-842.
Terao, et al., "Cryosurgery on Postganglionic Fibers {Poserior Nasal Branches) of the Pterygopalatine Ganglion for Vasomotor Rhinitis", Acta otolaryngol., vol. 96, 1983, pp. 139-148.

\* cited by examiner

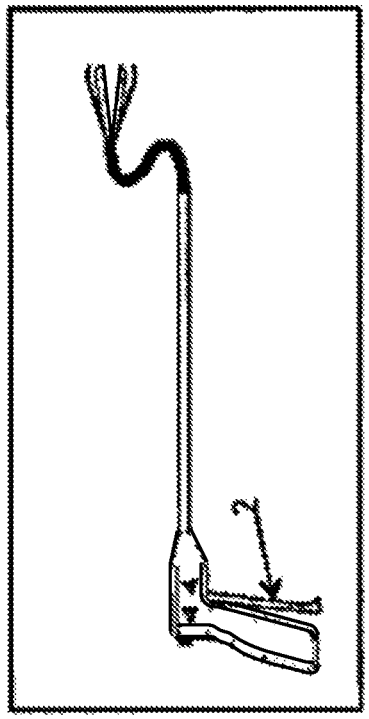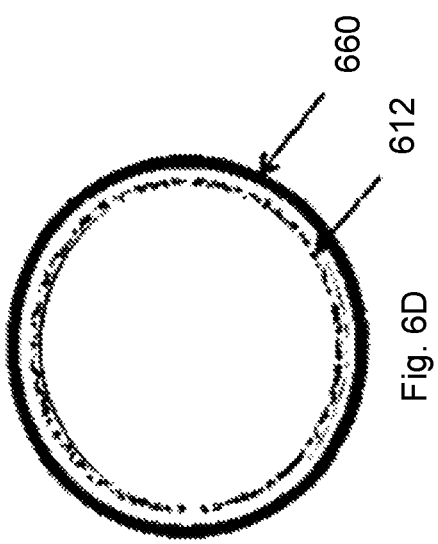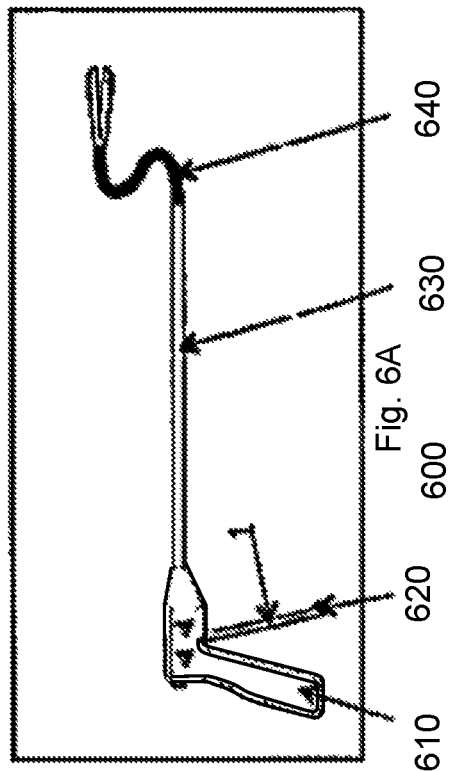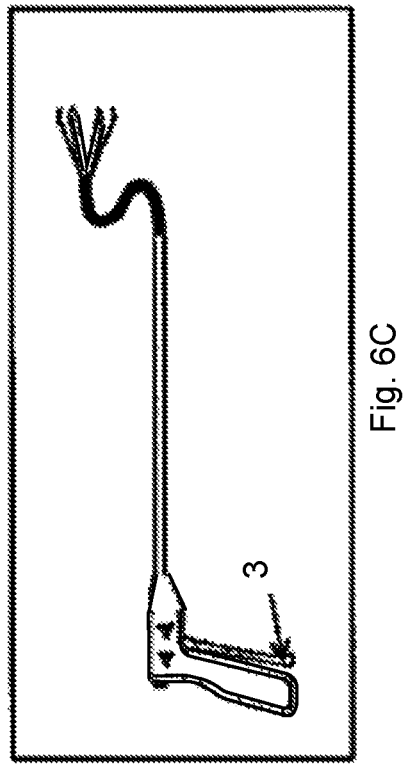
Fig. 6A
Fig. 6B
Fig. 6C
Fig. 6D

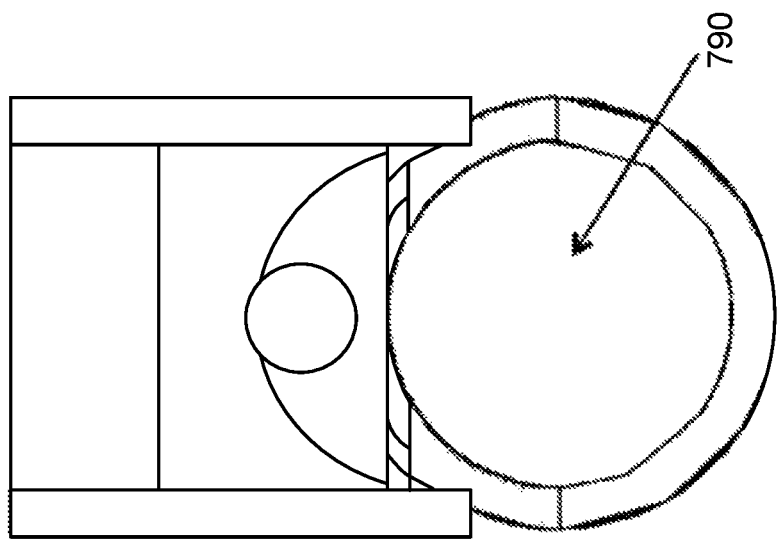

SURGICAL DEVICE WITH INTEGRATED VISUALIZATION AND CAUTERIZATION

CROSS-REFERENCE TO RELATED APPLICATIONS

This application is a continuation of U.S. patent application Ser. No. 14/957,475, filed Dec. 2, 2015, which is a continuation of U.S. patent application Ser. No. 14/168,717 filed Jan. 30, 2014, which claims the benefit of U.S. Provisional Application No. 61/762,660, filed Feb. 8, 2013, the content of which is incorporated herein by reference in its entirety.

BRIEF SUMMARY OF THE INVENTION

It is an object of this invention to provide a surgical device comprising a means for accessing a therapeutic target within a mammalian body, a means for creating space proximate to the therapeutic target, a means for visualizing the therapeutic target and surroundings, and a means for providing therapy.

In accordance with another aspect of this invention is a surgical device comprising a means for accessing a therapeutic target within a mammalian body, a means for creating space proximate to the therapeutic target, a means for visualizing the therapeutic target and surroundings, and a means for providing therapy, configured to access the therapeutic target through a natural bodily orifice.

In accordance with another aspect of this invention is a surgical device comprising a means for accessing a therapeutic target within a mammalian body, a means for creating space proximate to the therapeutic target, a means for visualizing the therapeutic target and surroundings, and a means for providing therapy, configured to access the therapeutic target through a surgically created orifice.

In accordance with another aspect of this invention is a surgical device comprising an elongated flexible structure comprising a distal end, a proximal end, and a central lumen; an expandable space-creating structure mounted in the vicinity of the distal end configured for placement within a mammalian body proximate to a therapeutic target, and a proximal terminal comprising an actuator mounted in the vicinity of the proximal end configured to remain outside of said body and provide the user with a means for actuating the space-creating structure, and at least one fluid connector, whereby said expandable structure comprises at least one expandable leaflet, and said central lumen is in fluidic communication between the interior of the expandable space-creating structure and the at least one fluid connector.

In accordance with another aspect of this invention is a surgical device comprising an elongated flexible structure comprising a distal end, a proximal end, and a central lumen; an expandable space creating structure mounted in the vicinity of the distal end configured for placement within a mammalian body proximate to a therapeutic target, and a proximal terminal comprising an actuator mounted in the vicinity of the proximal end configured to remain outside of said body and provide the user with a means for actuating the space-creating structure, and at least one fluid connector, whereby said expandable structure comprises at least one optically transparent expandable leaflet, and said central lumen is in fluidic communication between the interior of the expandable space-creating structure and the at least one fluid connector.

In accordance with another aspect of this invention is a surgical device comprising an elongated flexible structure comprising a distal end, a proximal end, and a central lumen; an expandable space-creating structure mounted in the vicinity of the distal end configured for placement within a mammalian body proximate to a therapeutic target, and a proximal terminal comprising an actuator mounted in the vicinity of the proximal end configured to remain outside of said body and provide the user with a means for actuating the space-creating structure, and at least one fluid connector, whereby said expandable space-creating structure comprises at least one optically transparent expandable leaflet, and at least one internally mounted imaging device, and said central lumen is in fluidic communication between the interior of the expandable space creating structure and the at least one fluid connector.

In accordance with another aspect of this invention is a surgical device comprising an elongated flexible structure comprising a distal end, a proximal end, and a central lumen; an expandable space-creating structure mounted in the vicinity of the distal end configured for placement within a mammalian body proximate to a therapeutic target comprising at least one optically transparent expandable leaflet, at least one internally mounted imaging device, and at least one internally mounted light emitting device, and a proximal terminal comprising an actuator mounted in the vicinity of the proximal end configured to remain outside of said body and provide the user with a means for actuating the expandable space-creating structure, and at least one fluid connector, whereby, said imaging device is a camera, and said light emitting device is an array of light emitting diodes, and the central lumen is in fluidic communication between the interior of the expandable space-creating structure and the at least one fluid connector.

In accordance with another aspect of this invention is a surgical device comprising an elongated flexible structure comprising a distal end, a proximal end, and a central lumen; an expandable space-creating structure mounted in the vicinity of the distal end configured for placement within a mammalian body proximate to a therapeutic target comprising at least one optically transparent expandable leaflet, at least one internally mounted imaging device, and at least one internally mounted light emitting device, and a proximal terminal comprising an actuator mounted in the vicinity of the proximal end configured to remain outside of said body and provide the user with a means for actuating the expandable space-creating structure, and at least one fluid connector, whereby, said imaging device comprises a coherent optical bundle, and the central lumen is in fluidic communication between the interior of the expandable space-creating structure and the at least one fluid connector.

In accordance with another aspect of this invention is a surgical device comprising an elongated flexible structure comprising a distal end, a proximal end, and a central lumen; an expandable space creating structure mounted in the vicinity of the distal end configured for placement within a mammalian body proximate to a therapeutic target comprising at least one optically transparent expandable leaflet, at least one internally mounted imaging device, and at least one internally mounted light emitting device, and a proximal terminal comprising an actuator mounted in the vicinity of the proximal end configured to remain outside of said body and provide the user with a means for actuating the expandable space-creating structure, and at least one fluid connector, whereby, said the aim of said imaging device is associated with the expansion of said leaflet, and the central lumen is in fluidic communication between the interior of the expandable space-creating structure and the at least one fluid connector.

In accordance with another aspect of this invention is a surgical device comprising an elongated flexible structure comprising a distal end, a proximal end, and a central lumen; an expandable space-creating structure mounted in the vicinity of the distal end configured for placement within a mammalian body proximate to a therapeutic target comprising at least one optically transparent expandable leaflet, two internally mounted imaging devices, and at least one internally mounted light emitting device, and a proximal terminal comprising an actuator mounted in the vicinity of the proximal end configured to remain outside of said body and provide the user with a means for actuating the expandable space-creating structure, and at least one fluid connector, whereby, said imaging devices are configured for three dimensional imaging, and the central lumen is in fluidic communication between the interior of the expandable space-creating structure and the at least one fluid connector.

In accordance with another aspect of this invention is a surgical device comprising an elongated flexible structure comprising a distal end, a proximal end, and a central lumen; an expandable space-creating structure mounted in the vicinity of the distal end configured for placement within a mammalian body proximate to a therapeutic target comprising at least one optically transparent expandable leaflet, at least one internally mounted imaging device, and a proximal terminal comprising an actuator mounted in the vicinity of the proximal end configured to remain outside of said body and provide the user with a means for actuating the expandable space-creating structure, and at least one fluid connector, whereby, said imaging device comprises and ultrasonic imaging transducer, and the central lumen is in fluidic communication between the interior of the expandable space-creating structure and the at least one fluid connector.

In accordance with another aspect of this invention is a surgical device comprising an elongated flexible structure comprising a distal end, a proximal end, and a central lumen; an expandable space-creating structure mounted in the vicinity of the distal end configured for placement within a mammalian body proximate to a therapeutic target, and a proximal terminal comprising an actuator mounted in the vicinity of the proximal end configured to remain outside of said body and provide the user with a means for actuating the space-creating structure, and comprises at least one fluid connector, and at least one electrical connector, whereby said expandable structure comprises at least one expandable leaflet comprising a radiofrequency electrode surface disposed in the vicinity of its edge, and in electrical communication with said at least one electrical connector, and said central lumen is in fluidic communication between the interior of the expandable space creating structure and the at least one fluid connector.

In accordance with another aspect of this invention is a surgical device comprising an elongated flexible structure comprising a distal end, a proximal end, and a central lumen; an expandable space-creating structure mounted in the vicinity of the distal end configured for placement within a mammalian body proximate to a therapeutic target, and a proximal terminal comprising an actuator mounted in the vicinity of the proximal end configured to remain outside of said body and provide the user with a means for actuating the space-creating structure, and comprises at least one fluid connector, and at least two electrical connectors, whereby said expandable structure comprises at least one expandable leaflet comprising a radiofrequency electrode surface disposed in the vicinity of its edge, a second electrode surface disposed in opposition to the first electrode surface with the first electrode surface in electrical communication with one electrical connector, and the second electrode surface in electrical communication with the second electrical connector, and said central lumen is in fluidic communication between the interior of the expandable space-creating structure and the at least one fluid connector.

In accordance with another aspect of this invention is a surgical device comprising an elongated flexible structure comprising a distal end, a proximal end, a central lumen, and at least one additional lumen; an expandable space-creating structure mounted in the vicinity of the distal end configured for placement within a mammalian body proximate to a therapeutic target, and a proximal terminal comprising an actuator mounted in the vicinity of the proximal end configured to remain outside of said body and provide the user with a means for actuating the space-creating structure, and comprises at least two fluid connectors, whereby said central lumen is in fluidic communication between the interior of the expandable space-creating structure and one fluid connector, and said at least one additional lumen is in fluidic communication with the second fluid connector, wherein the central lumen is configured for aspiration, and the second lumen is configured for irrigation.

In accordance with another aspect of this invention is a surgical device comprising an elongated flexible structure comprising a distal end, a proximal end, a central lumen, and at least one additional lumen; an expandable space-creating structure mounted in the vicinity of the distal end configured for placement within a mammalian body proximate to a therapeutic target comprising at least one expandable leaflet, and a proximal terminal comprising an actuator mounted in the vicinity of the proximal end configured to remain outside of said body and provide the user with a means for actuating the space-creating structure, and comprises at least two fluid connectors, whereby said central lumen is in fluidic communication between the interior of the expandable space-creating structure and one fluid connector, and said at least one additional lumen is in fluidic communication between the distal end of said expandable leaflet, and the second fluid connector, wherein the central lumen is configured for aspiration, and the second lumen is configured for irrigation.

In accordance with another aspect of this invention is a surgical device comprising an elongated flexible structure comprising a distal end, a proximal end, a central lumen, and at least one additional lumen; an expandable space-creating structure mounted in the vicinity of the distal end configured for placement within a mammalian body proximate to a therapeutic target comprising at least one expandable leaflet, and a proximal terminal comprising an actuator mounted in the vicinity of the proximal end configured to remain outside of said body and provide the user with a means for actuating the space-creating structure, and comprises at least two fluid connectors, whereby said central lumen is in fluidic communication between the interior of the expandable space-creating structure and one fluid connector, and said at least one additional lumen is in fluidic communication between the distal end of said expandable leaflet, and the second fluid connector, wherein the central lumen is configured for aspiration, and the second lumen is configured for hydrodissection.

In accordance with another aspect of this invention is a surgical device comprising an elongated flexible structure comprising a distal end, a proximal end, a central lumen, and at least one additional lumen; an expandable space-creating structure mounted in the vicinity of the distal end configured for placement within a mammalian body proximate to a therapeutic target comprising at least two opposing expandable leaflets, and a proximal terminal comprising an actuator mounted in the vicinity of the proximal end configured to remain outside of said body and provide the user with a means for actuating the space-creating structure, and comprises at least two fluid connectors, whereby said central lumen is in fluidic communication between the interior of the expandable space-creating structure and one fluid connector, and said at least one additional lumen is in fluidic communication between the distal end of each said expandable leaflet, and the second fluid connector, wherein the central lumen is configured for aspiration, and the second lumen is configured for hydro-dissection, wherein the hydro-dissection may be in a determined direction including distal, proximal, or lateral directions.

In accordance with another aspect of this invention is a surgical device comprising an elongated flexible structure comprising a distal end, a proximal end, a central lumen, and at least one additional lumen; an expandable space-creating structure mounted in the vicinity of the distal end configured for placement within a mammalian body proximate to a therapeutic target comprising at least one expandable leaflet, and a proximal terminal comprising an actuator mounted in the vicinity of the proximal end configured to remain outside of said body and provide the user with a means for actuating the space-creating structure, and comprises at least two fluid connectors, and a mechanical macerator disposed within the central lumen, whereby said central lumen is in fluidic communication between the interior of the expandable space-creating structure and one fluid connector, and said at least one additional lumen is in fluidic communication between interior of said expandable space-creating structure, and the second fluid connector, wherein said mechanical macerator is configured for maceration of tissue occupying the internal space of said expandable space-creating structure during therapy.

In accordance with another aspect of this invention is a surgical device comprising an elongated flexible structure comprising a distal end, a proximal end, a central lumen, and at least one additional lumen; an expandable space-creating structure mounted in the vicinity of the distal end configured for placement within a mammalian body proximate to a therapeutic target comprising at least one expandable leaflet, and a proximal terminal comprising an actuator mounted in the vicinity of the proximal end configured to remain outside of said body and provide the user with a means for actuating the space-creating structure, and comprises at least two fluid connectors, and a cryo-ablation probe disposed within the central lumen, whereby said central lumen is in fluidic communication between the interior of the expandable space-creating structure and one fluid connector, and said at least one additional lumen is in fluidic communication between interior of said expandable space-creating structure, and the second fluid connector, wherein said cryo-ablation probe is configured for cryo-ablation of tissue occupying the internal space of said expandable space-creating structure during therapy.

In accordance with another aspect of this invention is a surgical device comprising an elongated flexible structure comprising a distal end, a proximal end, a central lumen, and at least one additional lumen; an expandable space-creating structure mounted in the vicinity of the distal end configured for placement within a mammalian body proximate to a therapeutic target comprising at least one expandable leaflet, and a proximal terminal comprising an actuator mounted in the vicinity of the proximal end configured to remain outside of said body and provide the user with a means for actuating the space-creating structure, and comprises at least two fluid connectors, and a laser ablation disposed within the central lumen, whereby said central lumen is in fluidic communication between the interior of the expandable space-creating structure and one fluid connector, and said at least one additional lumen is in fluidic communication between interior of said expandable space-creating structure, and the second fluid connector, wherein said laser ablation probe is configured for laser ablation of tissue occupying the internal space of said expandable space-creating structure during therapy.

In accordance with another aspect of this invention is a surgical device comprising an elongated flexible structure comprising a distal end, a proximal end, a central lumen, and at least one additional lumen; an expandable space-creating structure mounted in the vicinity of the distal end configured for placement within a mammalian body proximate to a therapeutic target comprising at least one expandable leaflet, and a proximal terminal comprising an actuator mounted in the vicinity of the proximal end configured to remain outside of said body and provide the user with a means for actuating the space-creating structure, and comprises at least two fluid connectors, and a microwave ablation probe disposed within the central lumen, whereby said central lumen is in fluidic communication between the interior of the expandable space-creating structure and one fluid connector, and said at least one additional lumen is in fluidic communication between interior of said expandable space-creating structure, and the second fluid connector, wherein microwave ablation probe is configured for microwave ablation of tissue occupying the internal space of said expandable space-creating structure during therapy.

In accordance with another aspect of this invention is a surgical device comprising an elongated flexible structure comprising a distal end, a proximal end, a central lumen, and at least one additional lumen; an expandable space-creating structure mounted in the vicinity of the distal end configured for placement within a mammalian body proximate to a therapeutic target comprising at least one expandable leaflet, and a proximal terminal comprising an actuator mounted in the vicinity of the proximal end configured to remain outside of said body and provide the user with a means for actuating the space-creating structure, and comprises at least two fluid connectors, and a ultrasonic energy ablation probe disposed within the central lumen, whereby said central lumen is in fluidic communication between the interior of the expandable space-creating structure and one fluid connector, and said at least one additional lumen is in fluidic communication between interior of said expandable space-creating structure, and the second fluid connector, wherein said ultrasonic energy ablation probe is configured for ultrasonic energy ablation of tissue occupying the internal space of said expandable space-creating structure during therapy.

BRIEF DESCRIPTION OF THE DRAWINGS

FIGS. 6A-6D show a device for actuation of the subject invention.

FIGS. 7A-7D show another embodiment where the device is constructed of a metallic or hard polymer to allow it to puncture the skin of an individual.

DETAILED DESCRIPTION OF THE INVENTION

Figure 1A:
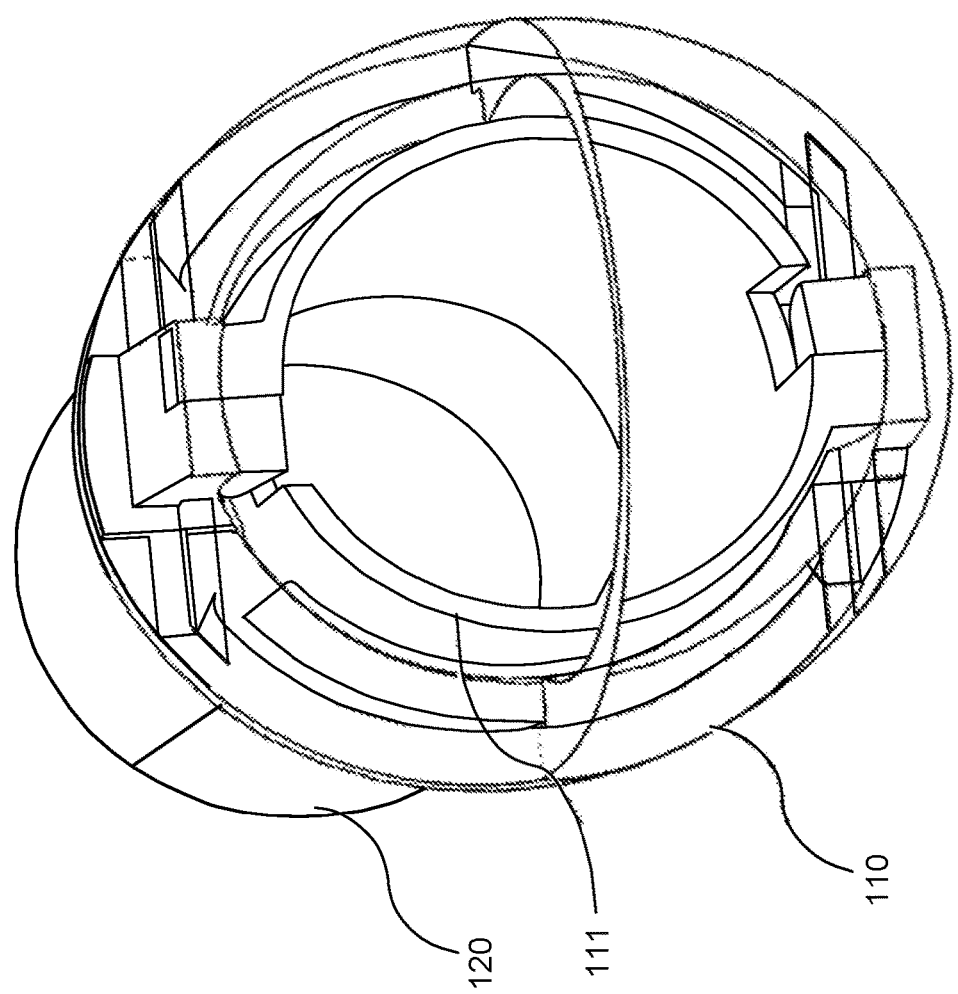
FIGS. 1A-1C show perspective views of a bi-leaflet embodiment of the present invention.
Figure 1B:
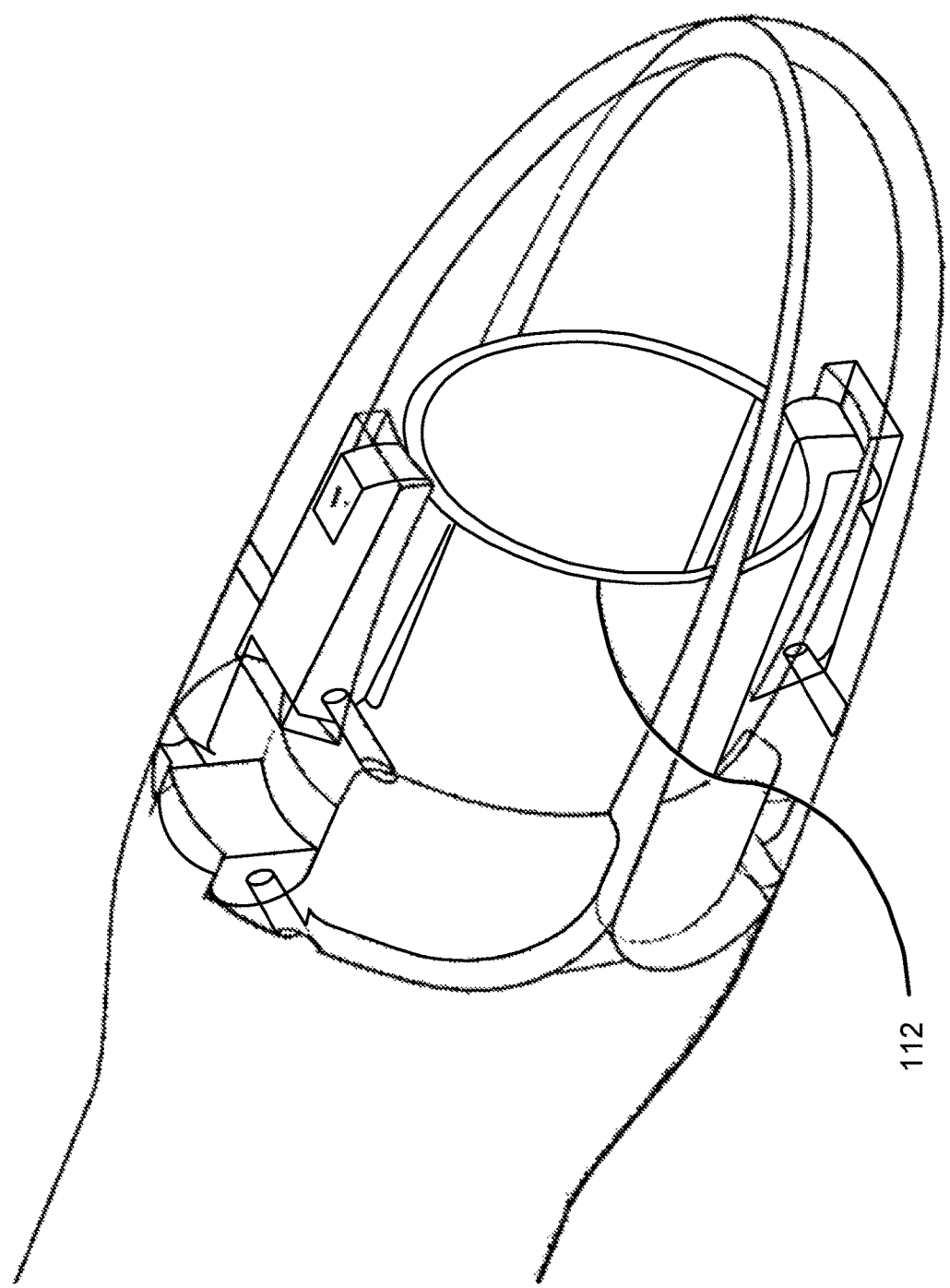
Figure 1C:
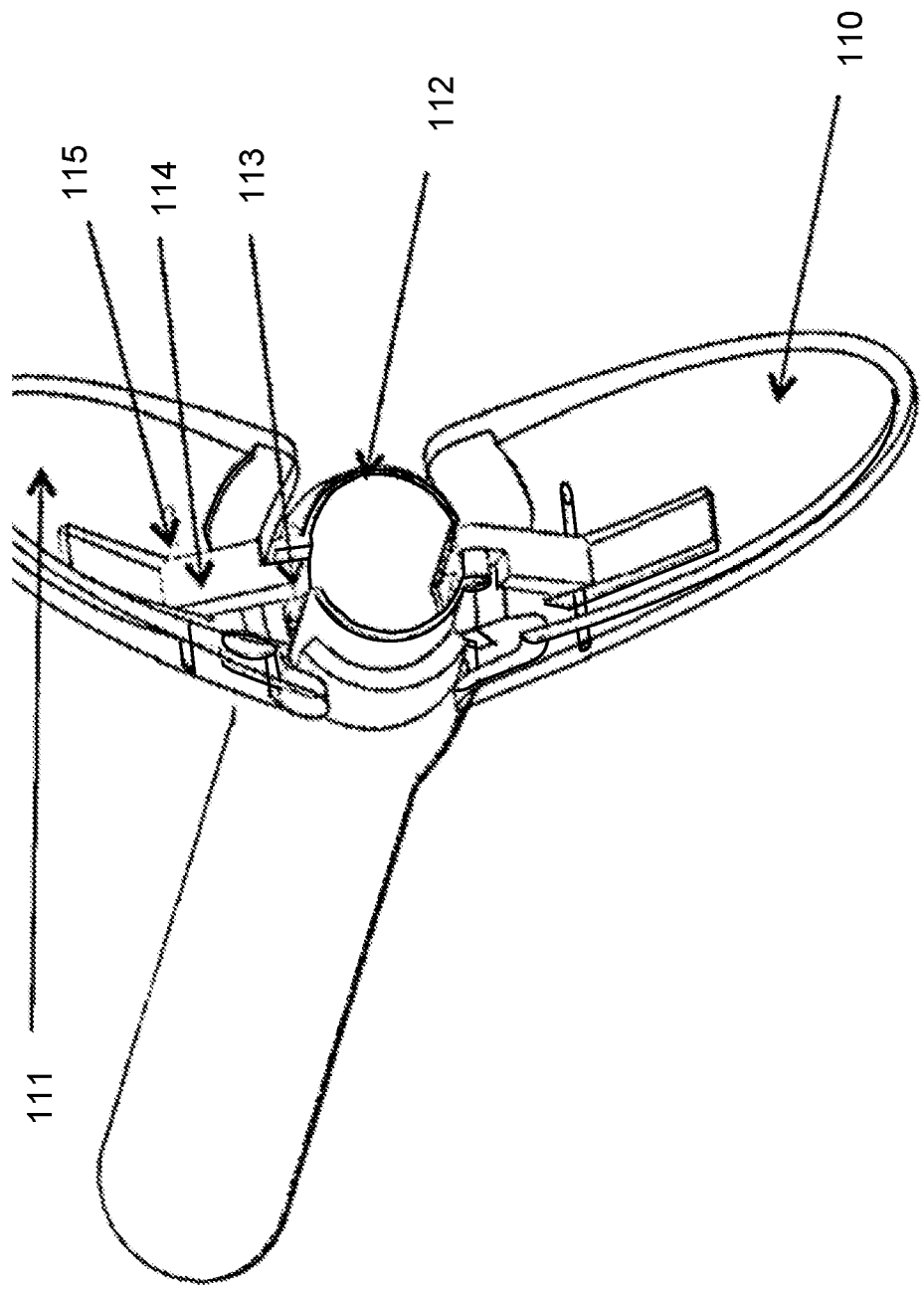

FIGS. 1A-1C show a bi-leaflet embodiment of the present invention. In FIG. 1A the two leaflets are identified as elements 110 and 111. Either one or both of these leaflets can be made transparent or translucent for a visualizing element, which might be inserted in the outer sheath 120 of the device to see through these leaflets and provide guidance for the operator while travers in the tissue to get to a target site. This visualizing element can be a rigid or flexible endoscope, a digital micro camera like the ones that Medigus or Awaiba markets, it could also be a fiber optic image bundle or any other image-carrying device. Transparent or translucent leaflets make visualization thru closed leaflets possible.

FIG. 1B shows another view of the present invention where the inner tube 112 is visible through the transparent leaflets. As this inner tube, 112 moves forward, it acts upon the leaflets 110 and 111 pushing them outward as explained below in FIG. 1C.

As FIG. 1C illustrates, the bi-leaflet structure is actuated and opened in an outward direction in order to achieve the desired tissue dilation and visualization. Element 112 is a tube tightly fitting within the outer sheath 120 and is in turn connected to the arm 114 through hinge 113. The arm 114 is in turn connected to the leaflet 111 through hinge 115. Forward motion of the tube 112 in cooperation with elements 113, 114, and 115 places an outward force on leaflet s 110 and 111 leading to their movement away from the central axis of the sheath 120. This force will be modulated by the mechanical advantage within the handle of the device to maintain a constant dilation force by the leaflet.

Figure 2A:
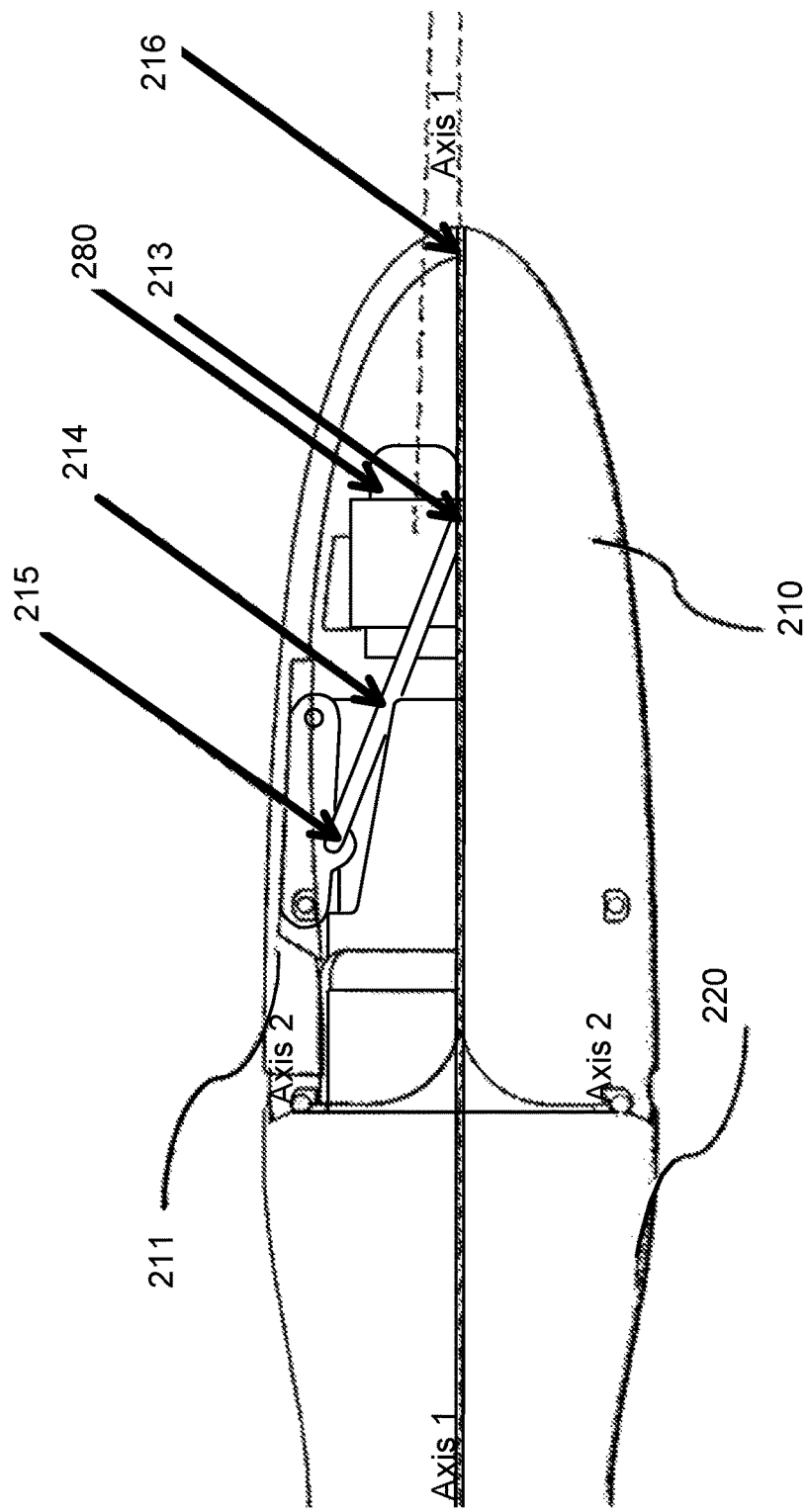
FIGS. 2A-2D show side and end views of another embodiment where a camera is mounted within the transparent or translucent space of a leaflet.
Figure 2B:
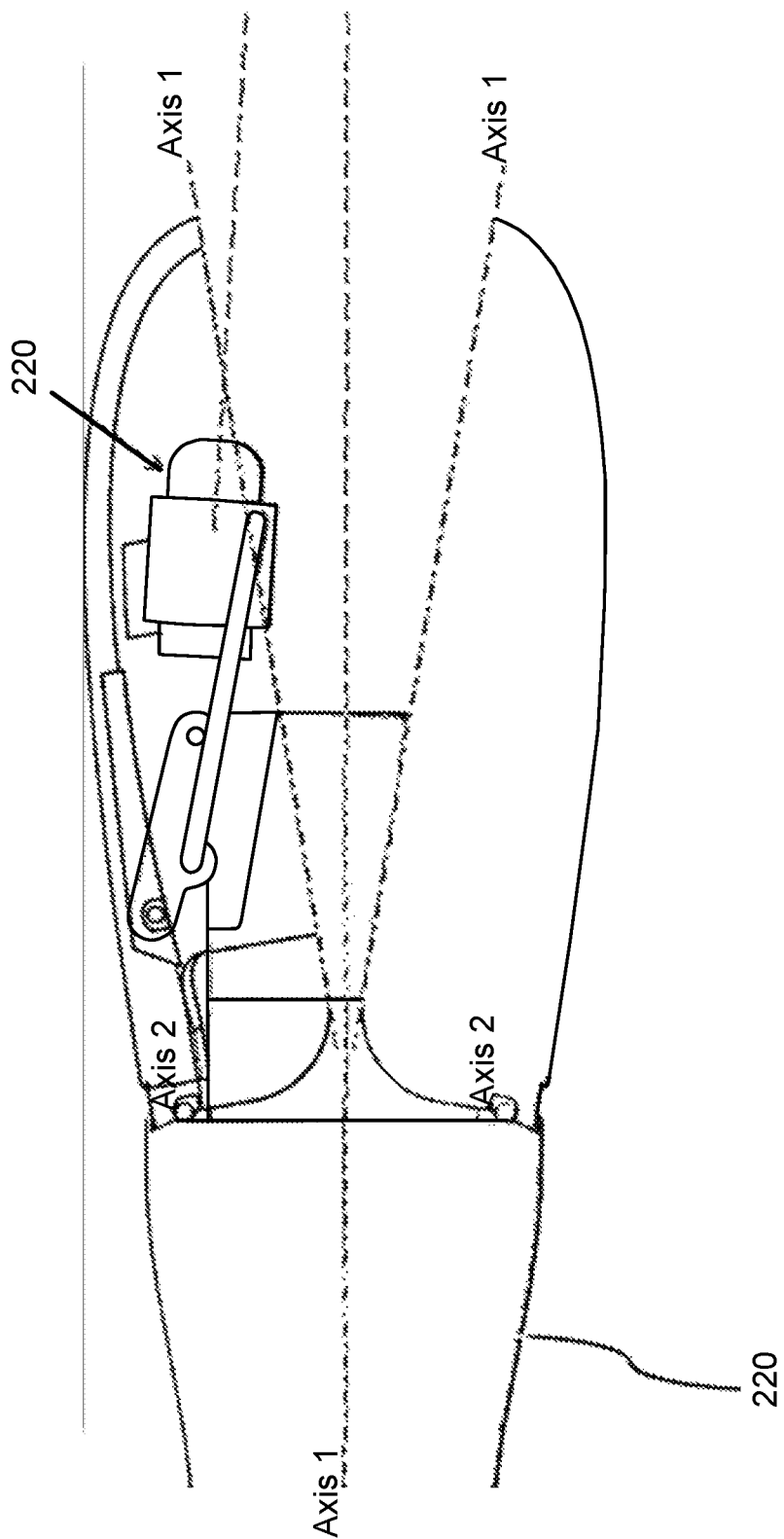

FIG. 2A shows another embodiment of the current invention where a camera 280 is mounted within the transparent or translucent space of leaflet 211 and looks forward through the leaflet 211 long the optical axis 216, in a somewhat paraxial arrangement. Camera 280 is connected to the top leaflet, 211 through arm 214 and arm 214 in turn is connected to the leaflet and camera through hinges 213 and 215. FIG. 2B shows the current embodiment with the leaflets slightly opened. Camera 280 is now looking slightly downward towards the central axis of the sheath 220.

Figure 2C:
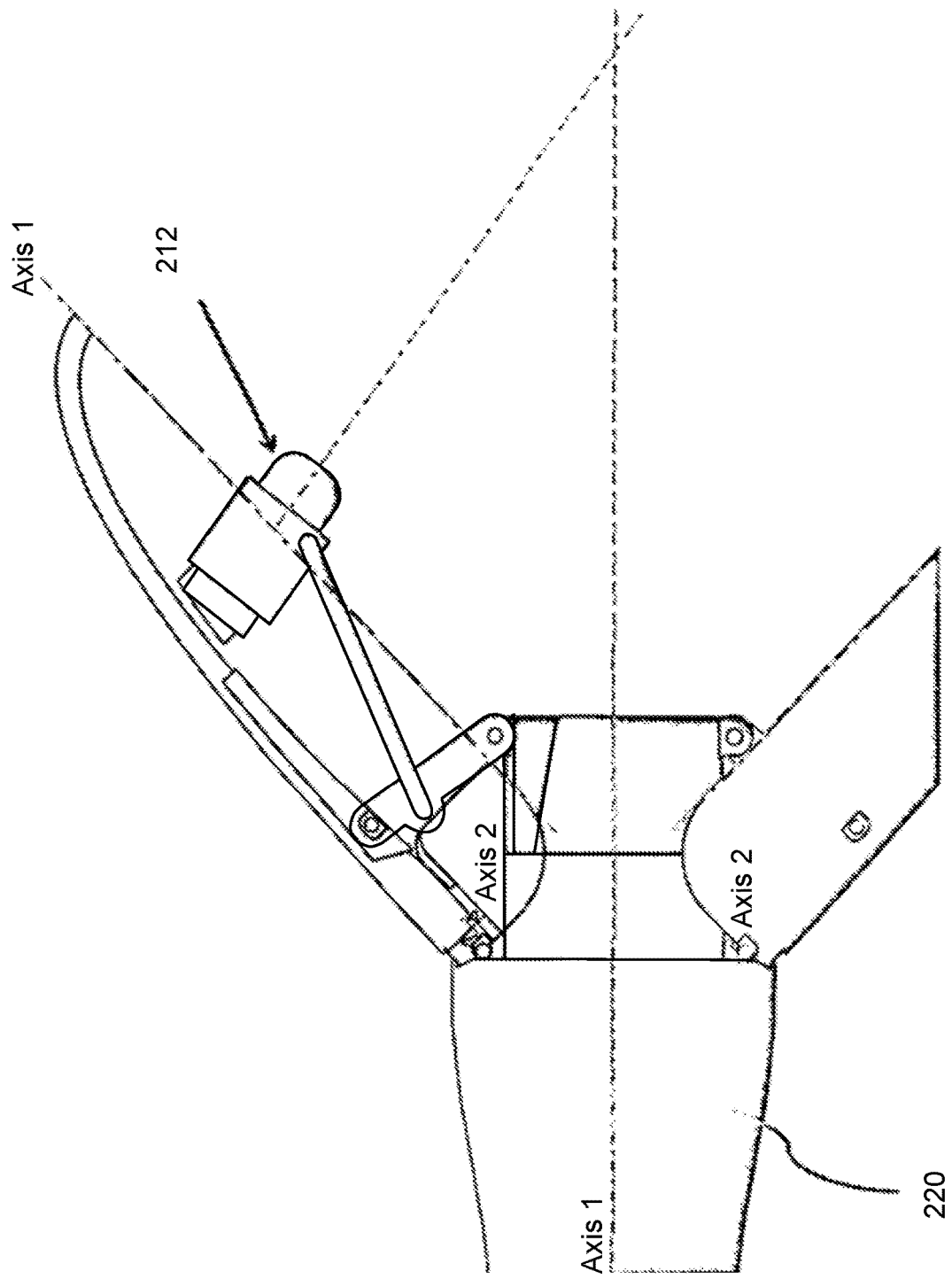
Figure 2D:
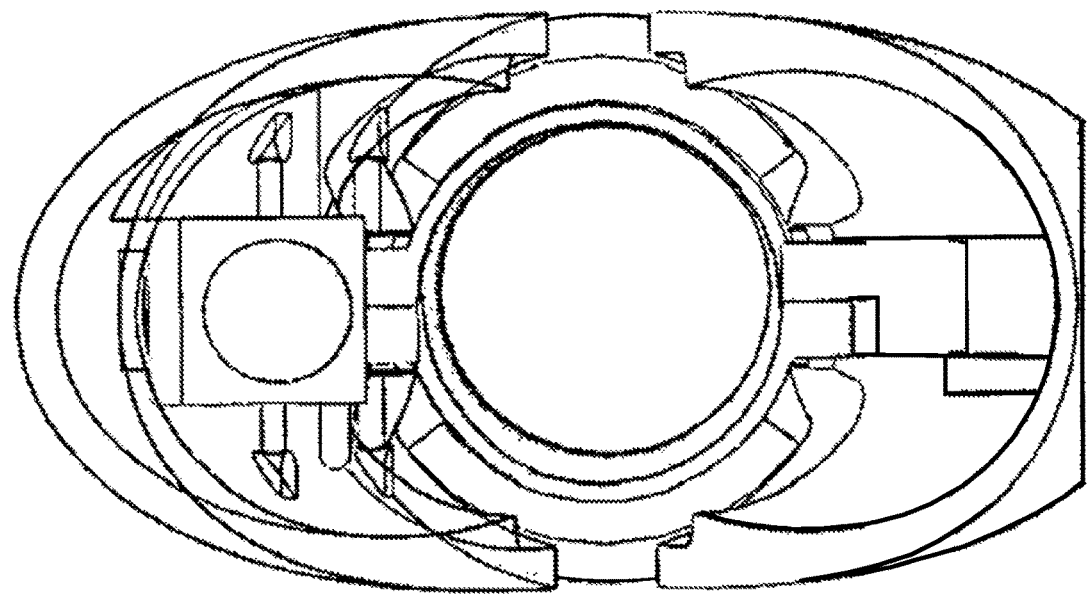

FIG. 2C illustrates further opening of the leaflets and now camera 28 is looking even further inward toward the optical axis and thereby provides a more relevant image to the operator who is interested in the tissue that is closer to the opening of the device. FIG. 2D is a front view of the subject invention illustrating the full lumen access upon opening of the leaflet as was mentioned before.

Figure 3A:
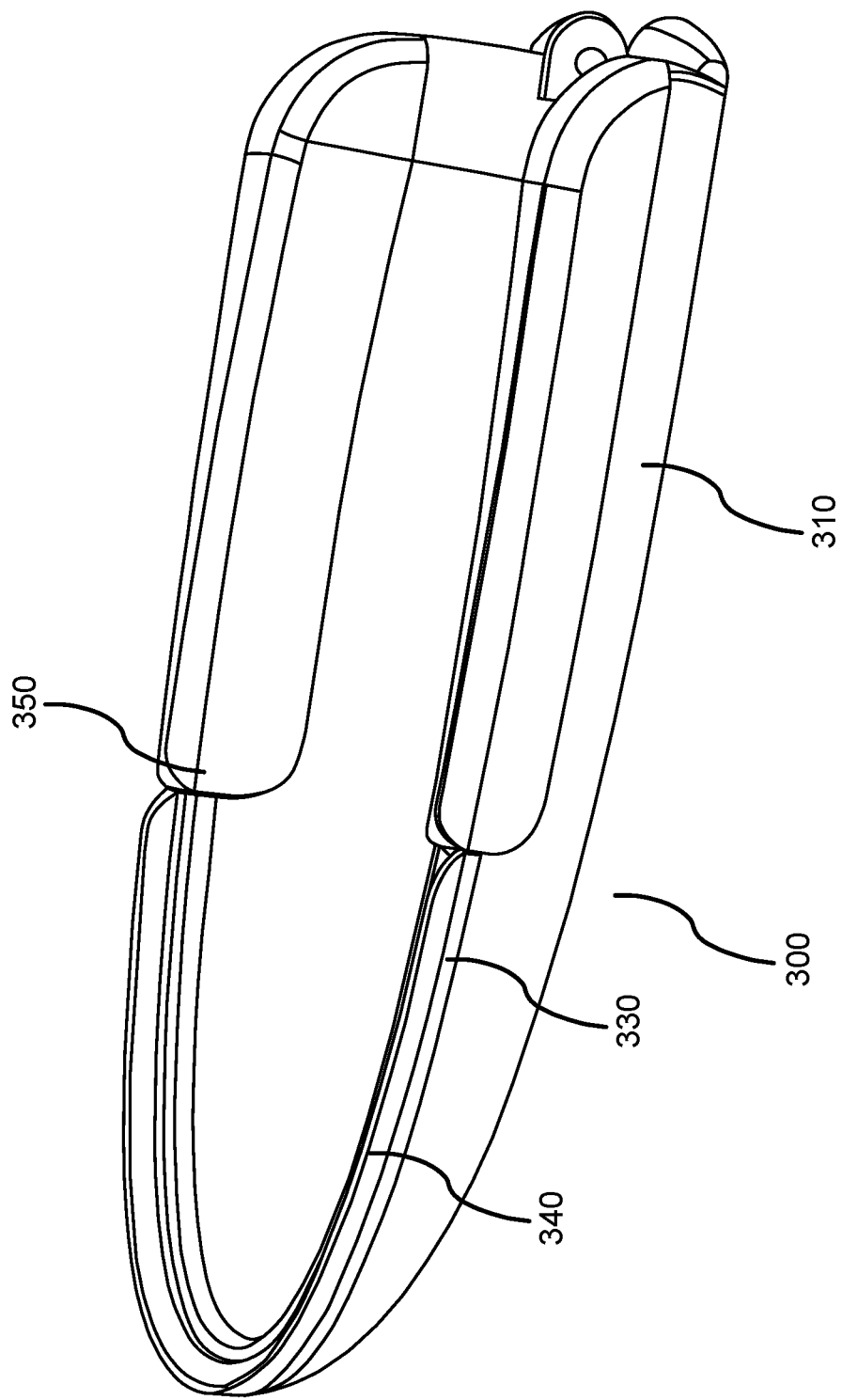
FIGS. 3A-3C perspective views of a lower leaflet that is capable of performing ablation and cauterization of the tissue.

FIG. 3A shows the lower leaflet of the subject invention, 300 that is capable of performing ablation and cauterization of the tissue. This embodiment of the subject invention is intended to take a partial bite of the tissue, which makes it easier to remove the dissected tissue that would be contained within the space between the two leaflets when the leaflets are closed and the tissue that's contained between the leaflets is separated from the surrounding area and the leaflets are touching alongside their length. In procedures where the operator is dependent on the clear visualization, cauterizing of the remaining surface of the dissected tissue prevents bleeding and creating turbidity in the irrigating fluid and thereby clouding the view. The leaflet can be made out of many different materials as described before.

Element 310 represents the lower leaflet that could be metallic or transparent or translucent as described before. Element 340 represents the portion of the lower leaflet which is conducive to electrical energy and in cooperation with the upper leaflet is utilized to resect the tissue by radio frequency. Element 330 is a high temperature non-conductive material with an expansion coefficient that is properly chosen to minimize the relative motion between elements 310, 330, 340. Examples of such materials include ceramics, polyimide, polysulfone, silicone, and other materials that have the qualities that were described.

Element 340, is a conductor chosen from the metallic group of materials or conductive polymer materials. This element will be electrically connected to a source of energy that would be used to cut and cauterize tissue. There is an identical element to 340, identified as 341, which is located on the upper leaflet. Elements 340 and 341 could also be made out of a fiber optic that can be connected to a source of high power laser so the tissue is optically cut and cauterized as known in the art. When electrical energy applied to ablate and cauterize the tissue a radiofrequency generator might be utilized to supply the required energy to this element which would in turn conduct this energy through the tissue and by the virtue of ohmic resistance of the tissue heat the tissue up to very high temperature quickly and thereby vaporize the intervening tissue between elements 340 on the lower leaflet and element 341, its mating part on the upper leaflet, 341. In case of and RF energy source that is bipolar as known in the art, conduction of energy occurs between these two elements, the upper and lower leaflets (340, 341). One can also utilize a mono-polar source of RF energy, which would be connected to both elements 340, 341 with a single wire and would require a reference patch at a remote location on the patient's body to complete the circuit.

Element 350 identifies an insulator which could be made out of hard foam, silicone, cork, acrylic, 335 polycarbonate and similar materials. Element 340 is a conductive metallic structure that has a sharp tip in the direction of the opposite leaflet. Element 330 is the insulator as described previously.

Figure 3B:
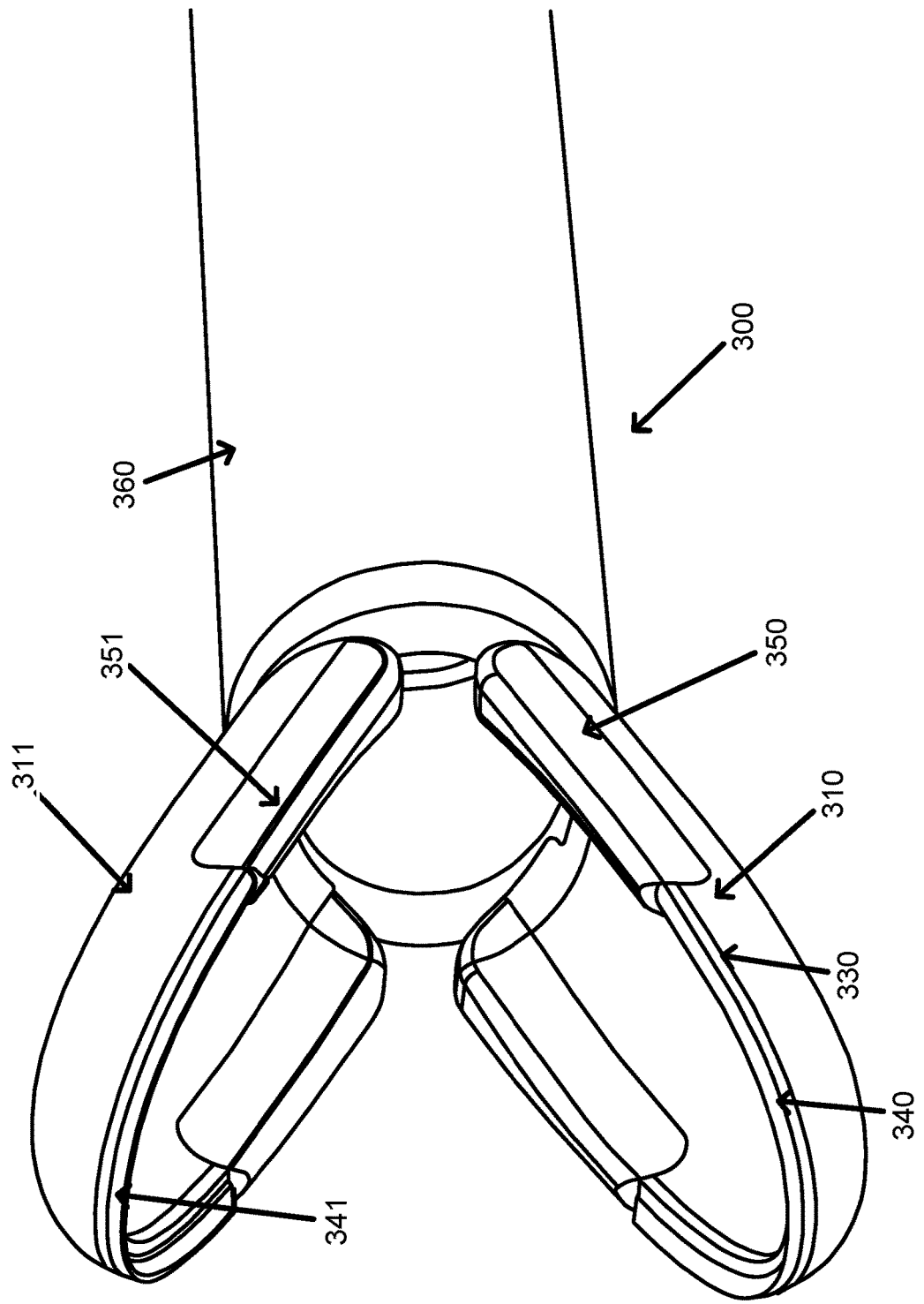

FIG. 3B shows the current invention with both leaflets 310 and 311 in the open position. The sheath 360 is connected to these leaflets through the hinges and arms as previously described.

Figure 3C:
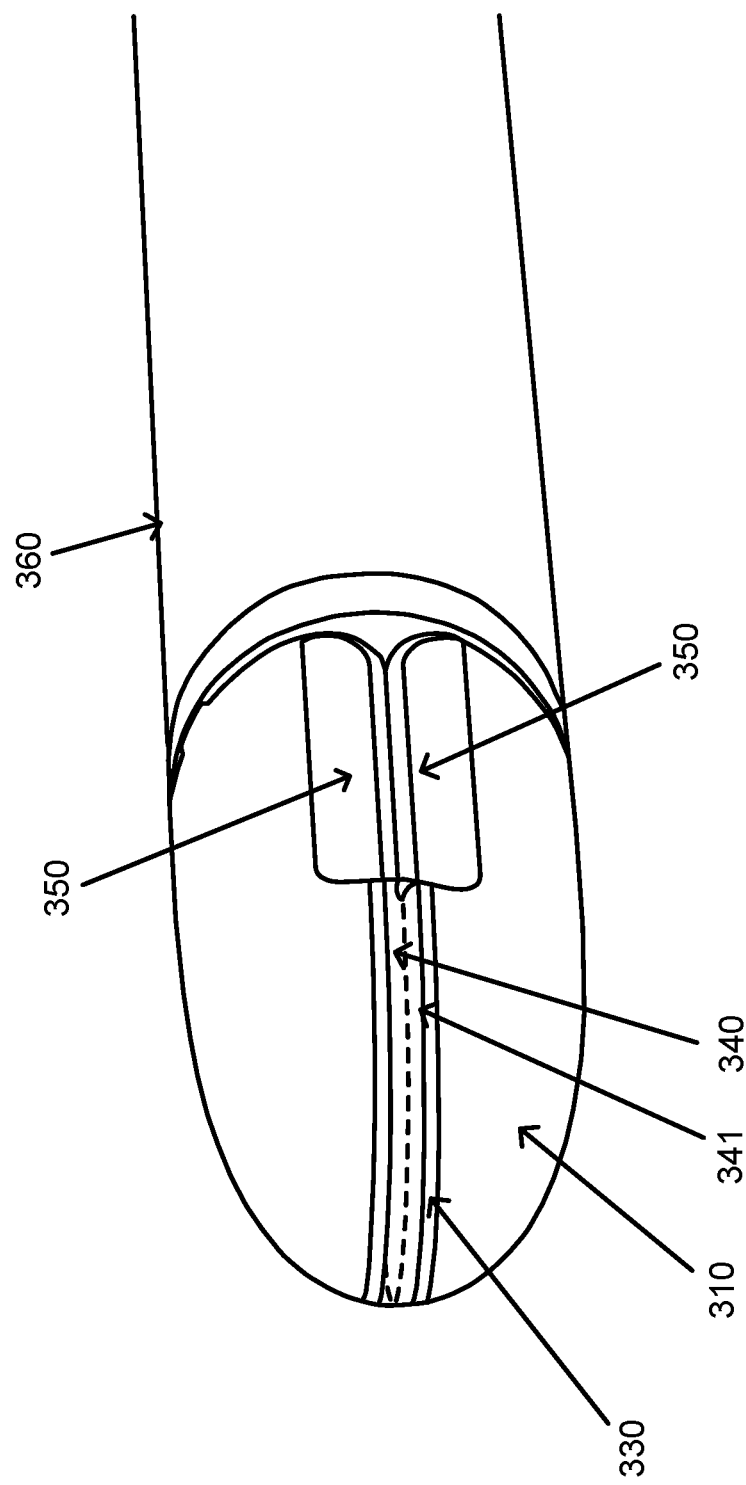

FIG. 3C one can see both leaflets in a closed position. The conductive elements 340 and 341 are contiguous or adjacent with very close proximity. Elements 350 and 351 show the insulating material as described the benefit of this insulating material is evident in this figure in as much as they prevent premature contact of the two blades when the energy source is of a Bipolar nature and also they limit the size of the tissue that is resected with each closure of the leaflets.

Figure 4A:
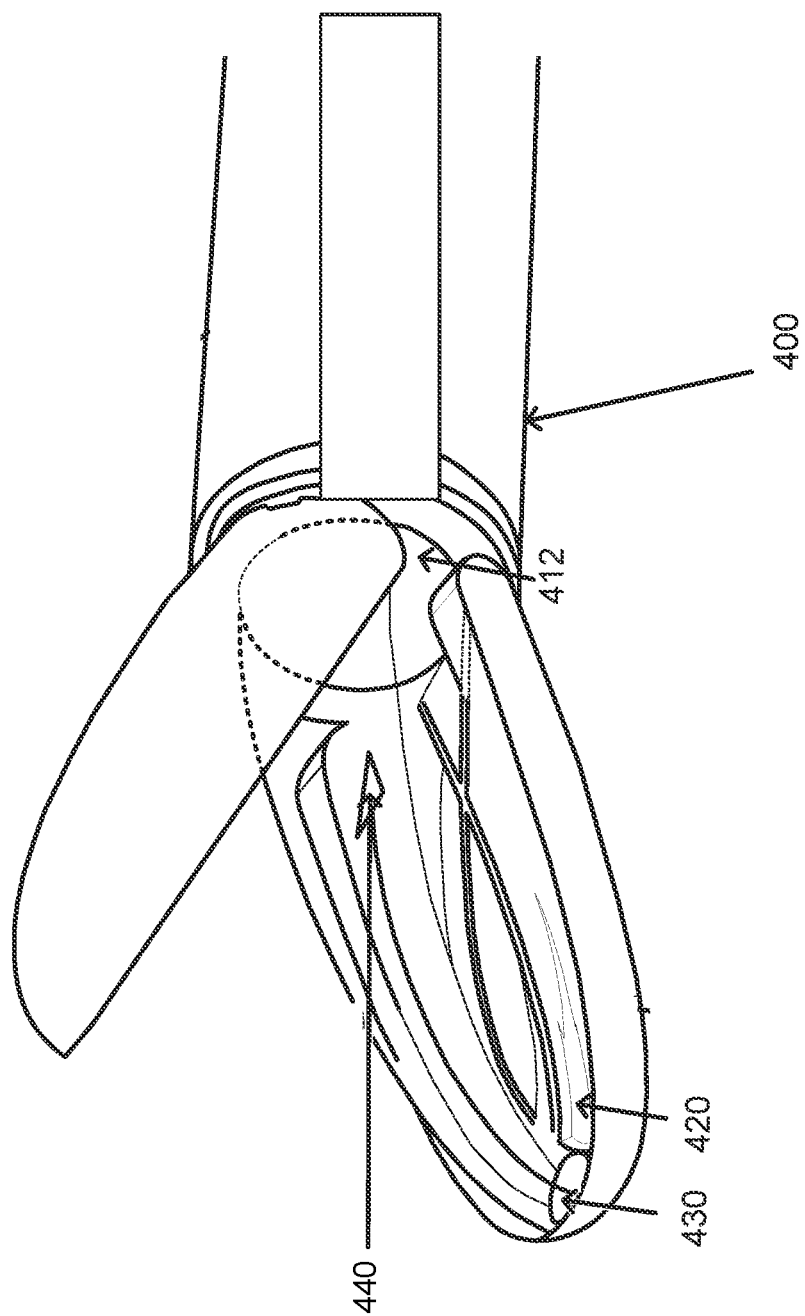
FIGS. 4A and 4B show perspective views of another embodiment incorporating fluid irrigation.

FIG. 4A shows the device 400 of the current invention incorporating irrigation and aspiration. Lumen 420 carries the irrigating fluid to the source outside the device at an appropriate pressure to the opening 430 where the irrigating fluid exits and through the inner tube 412 is aspirated. The arrow 440 shows the direction of the flow of the irrigating fluid.

Figure 4B:
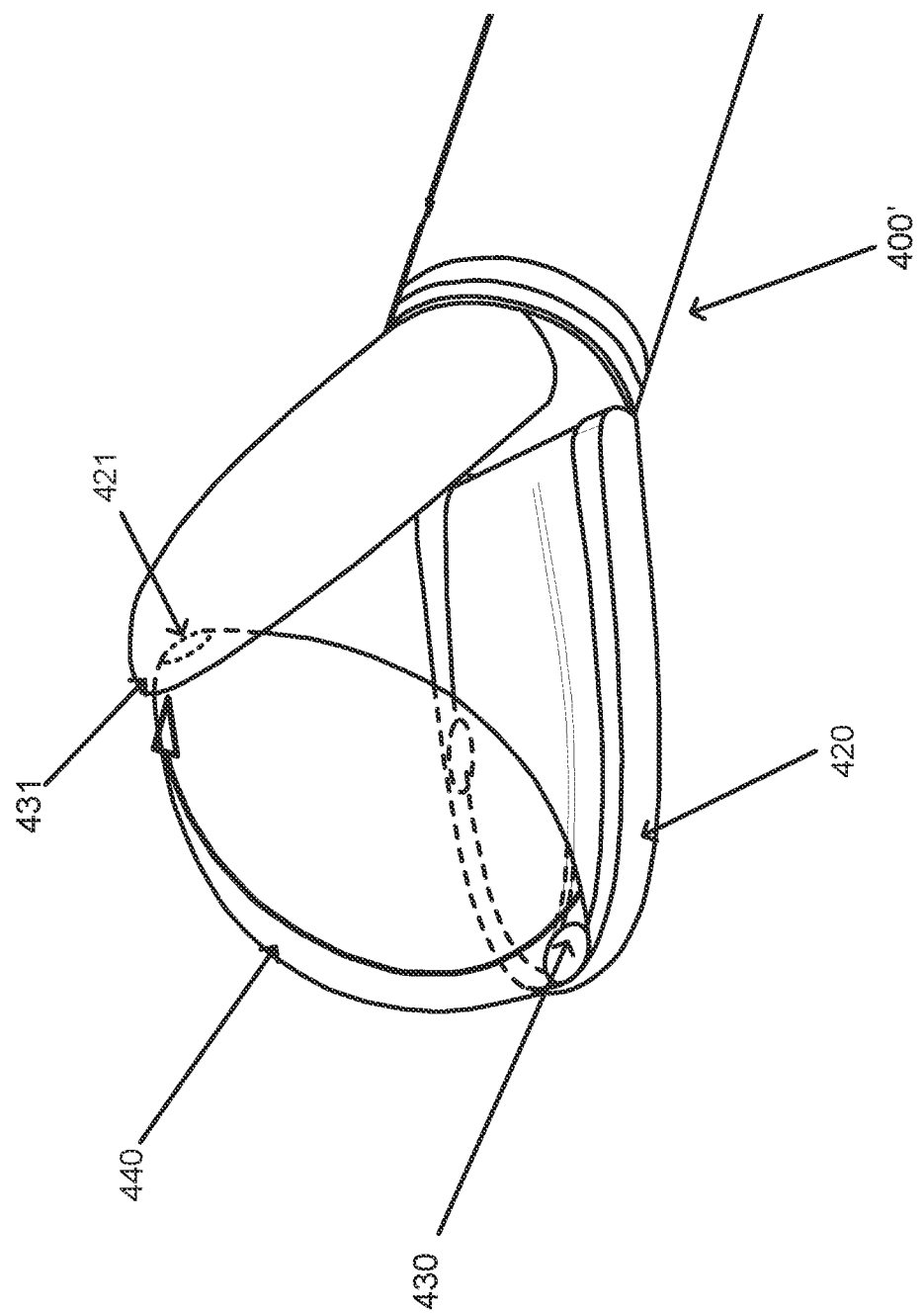

FIG. 4B shows another embodiment 400' of the current invention incorporating fluid irrigation where the path of the fluid is between openings 430 and 431 carried by lumens 420 and 421. Arrow 440 shows the direction of the flow of the fluid between openings 430 and 431. This embodiment of the current invention will provide the benefit of clearing of the operating area from blood and debris with a fluid flow path that extends beyond the distal end of the device.

Figure 5A:
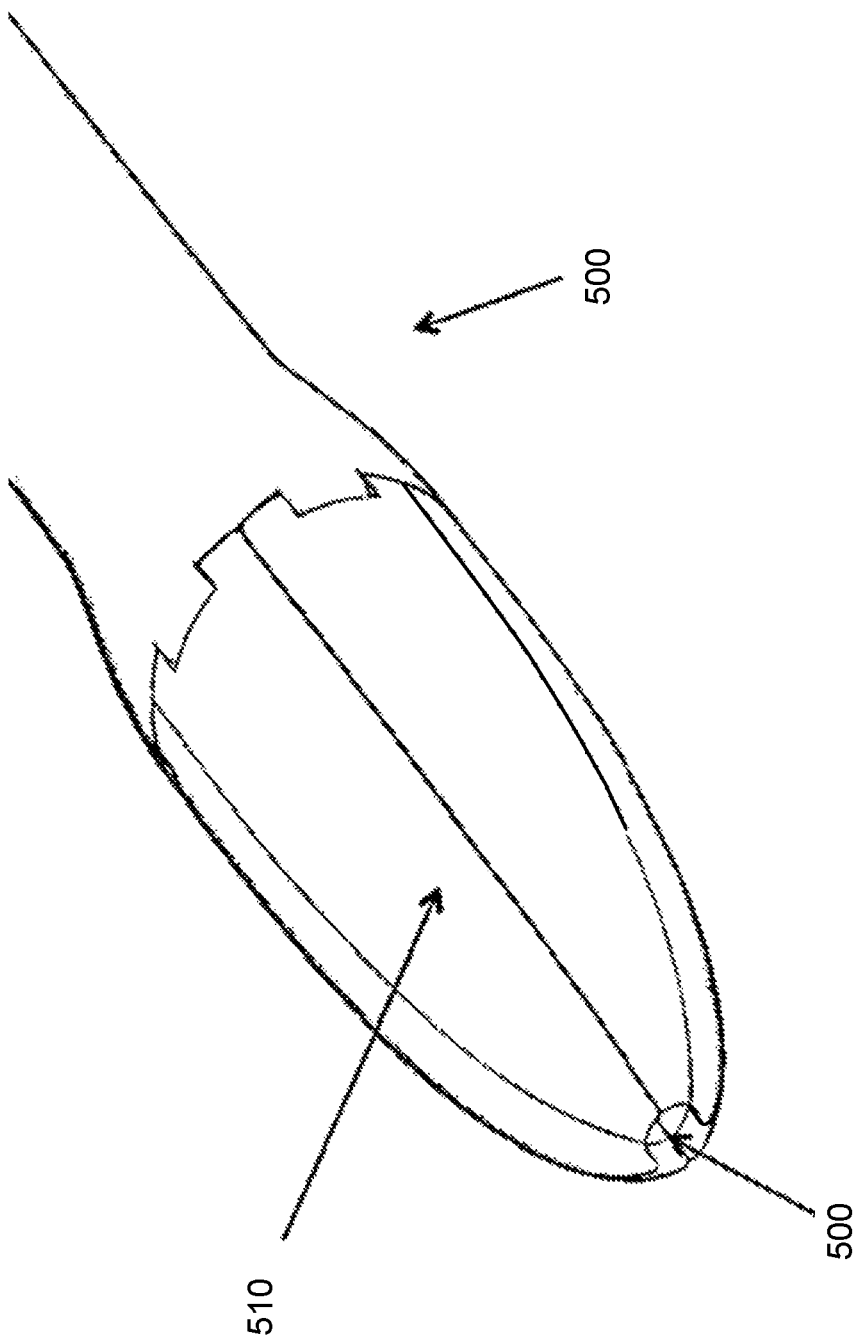
FIGS. 5A-5C show another embodiment with a plurality of leaflets.

FIG. 5A shows yet another embodiment of the subject invention with a plurality of leaflets which is comprised of 6 leaflets in this embodiment. This embodiment also incorporate an opening 590 which when the leaflets are in the closed position to provide a path to follow a guide wire that may have been inserted through the path of the interest to make it easier for this embodiment of the device to navigate through the tissue to the target.

Figure 5B:
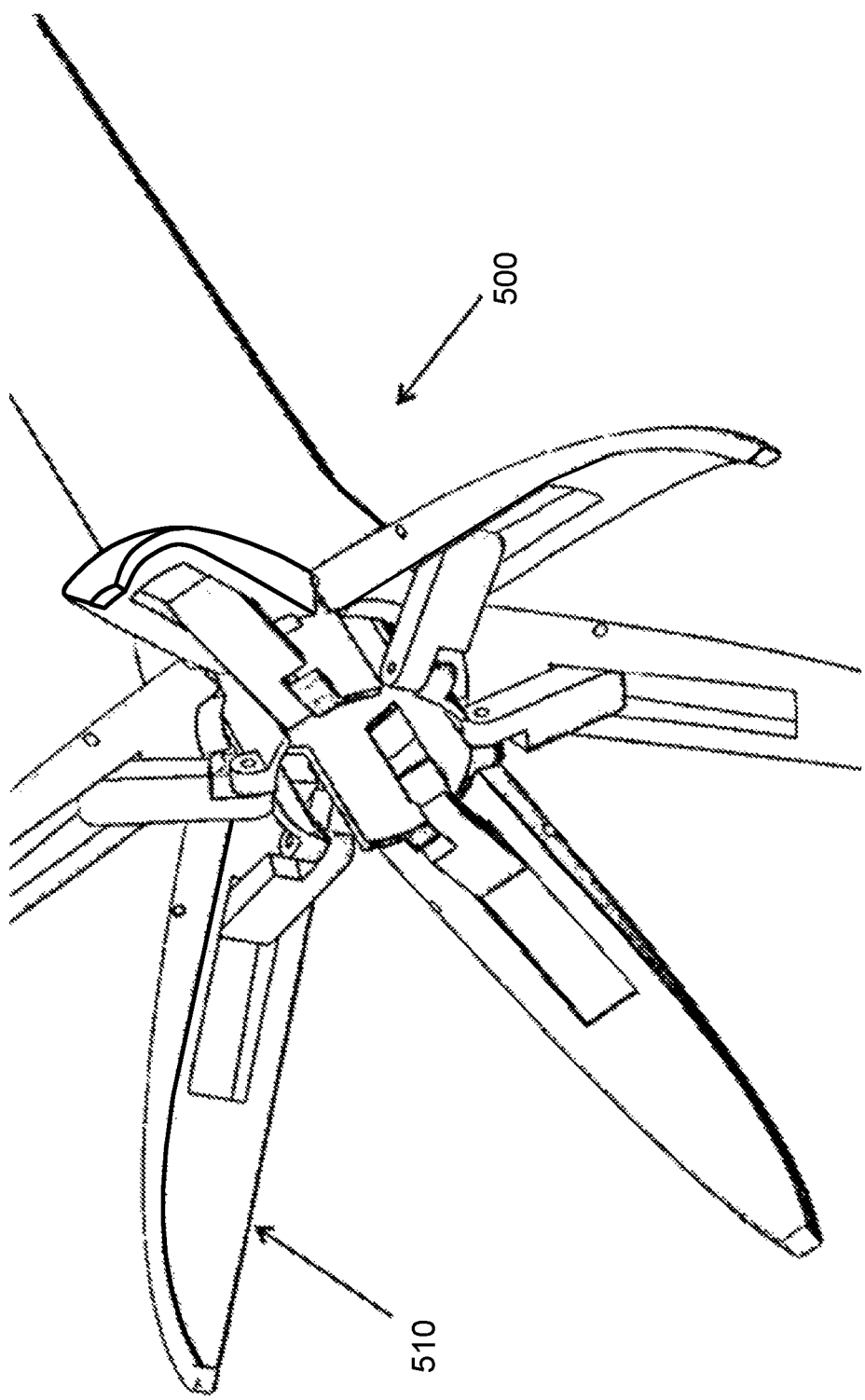

FIG. 5B shows the device of the FIG. 5A in an open position. The mechanism of opening of each of these leaflets can be inferred from FIG. 1C.

Figure 5C:
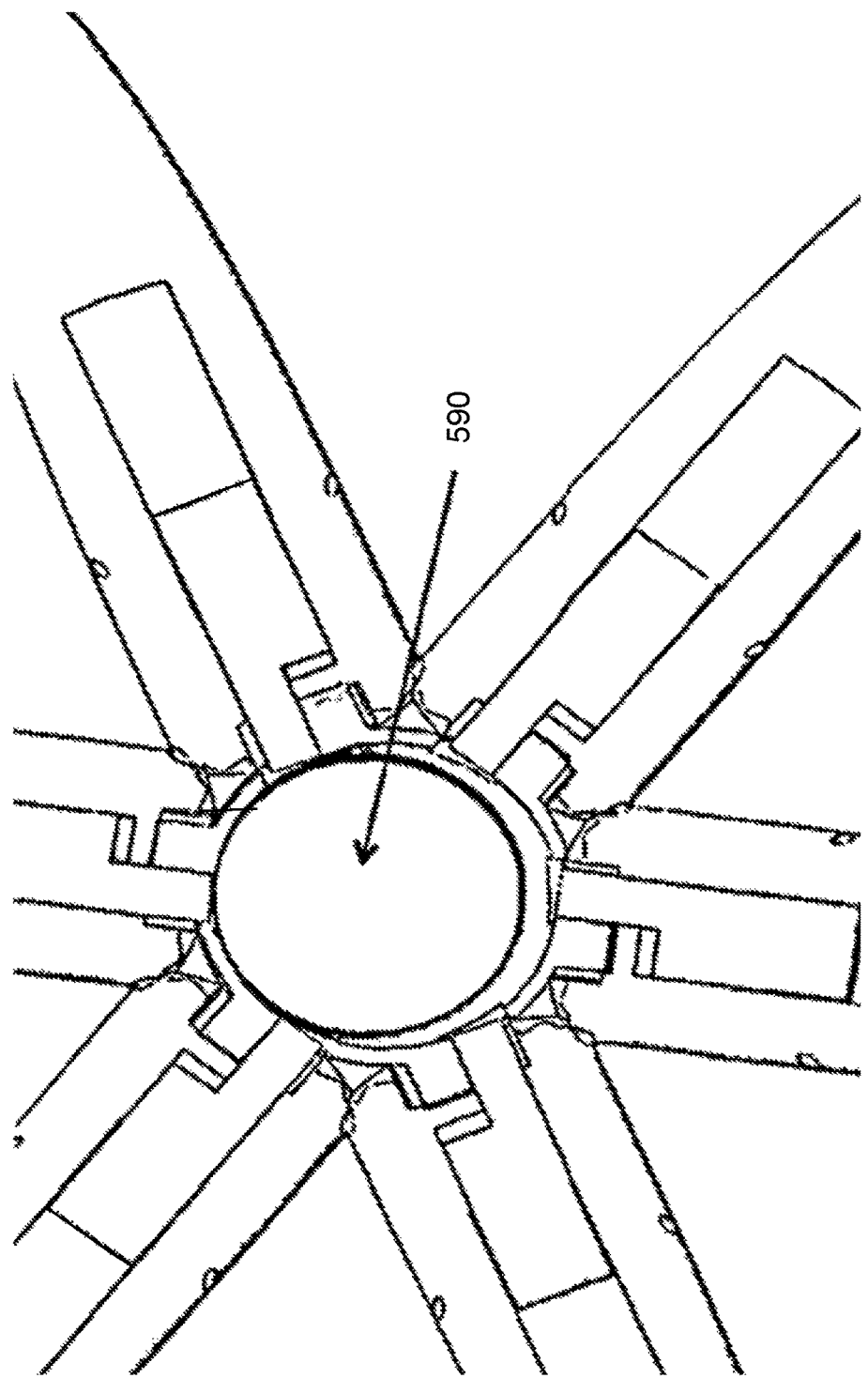

FIG. 5C shows the device in a completely open position accentuating the fact that the main lumen of the device 580 is unobstructed and fully available for passing of the tools of interest.

FIG. 6, A through C show a device for actuation of the subject invention which includes a handle 610, a trigger 620, a shaft 630 a flexible section 640, and a distal end effector 650. Figures A through C show the sequential movement of the trigger 620 and the opening of the end effector 650 further and further with the gradually increasing pressure applied to the trigger 620. As this increasing pressure is being applied, where the trigger moves between positions 1, 2, and 3 the distal multi leaflet structure opens wider and wider. Outer tube 660 contains an inner flexible tube 612, which is shown in FIG. 6D in the cross sectional, view. Tube 612 is flexible enough to follow the flexible section, 640 of this device.

FIG. 6D shows the relationship of the outer tube 660 and the inner tube 612. The tube 612 and 660 are chosen such that the inner diameter of the tube 660 closely matches the outer diameter of the flexible tube 612 in order to prevent undesirable movement from tube 612 while maintaining a small gap to allow relative longitudinal motion between these tubes.

Figure 7A:
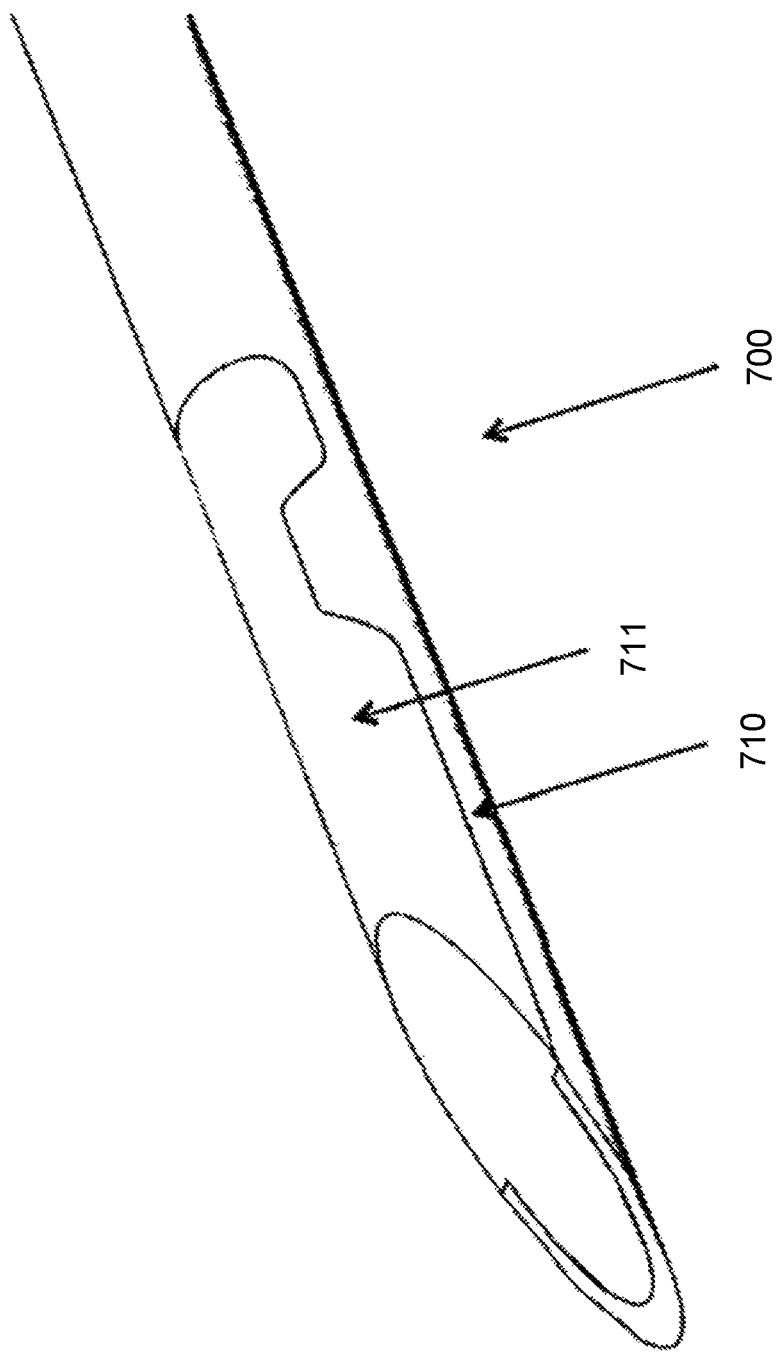

FIG. 7A shows another embodiment of the subject invention where the device is constructed of a metallic or hard polymer to allow it to puncture the skin of an individual. The lower leaflet of the device 700, which is identified 710, is made rigid to have high column strength in order to make it easier to penetrate the skin like a common hypodermic needle. The upper leaflet 711 is hinged to the body of the device.

Figure 7B:
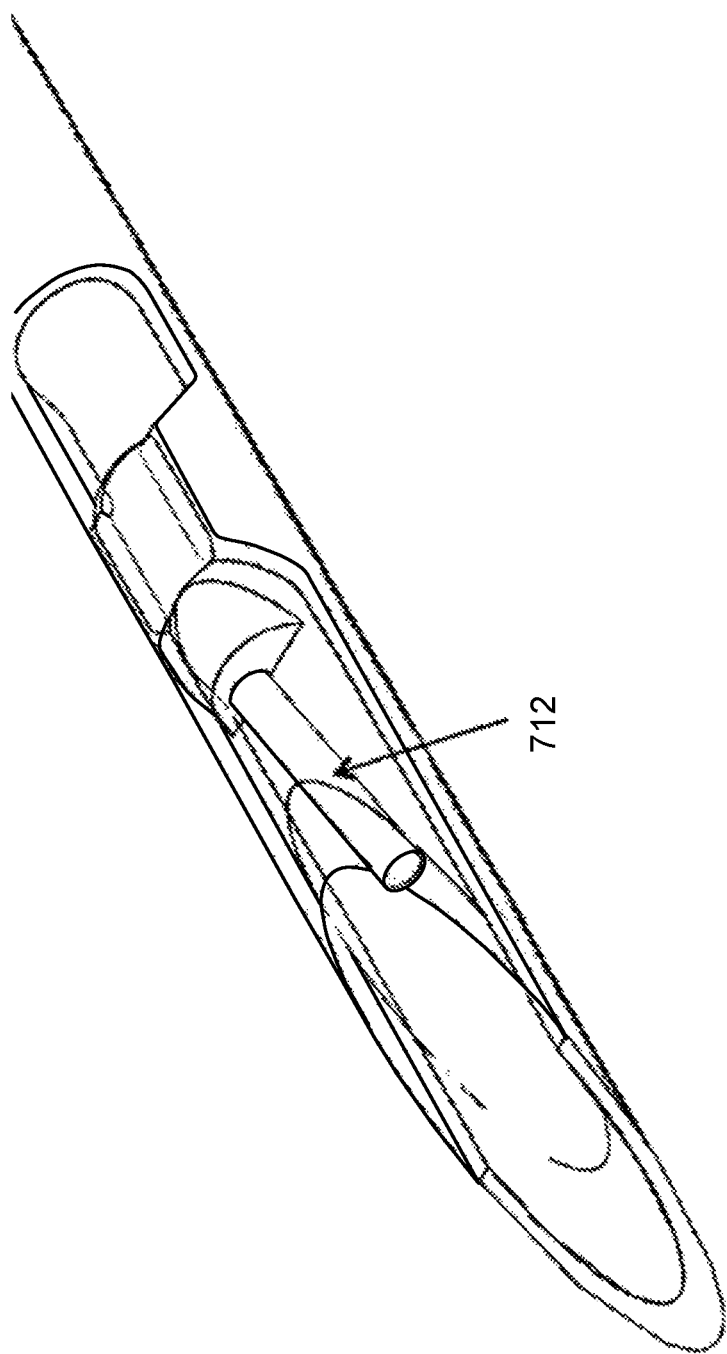

FIG. 7B shows the position of the camera within the upper leaflet 711 of the device.

Figure 7C:
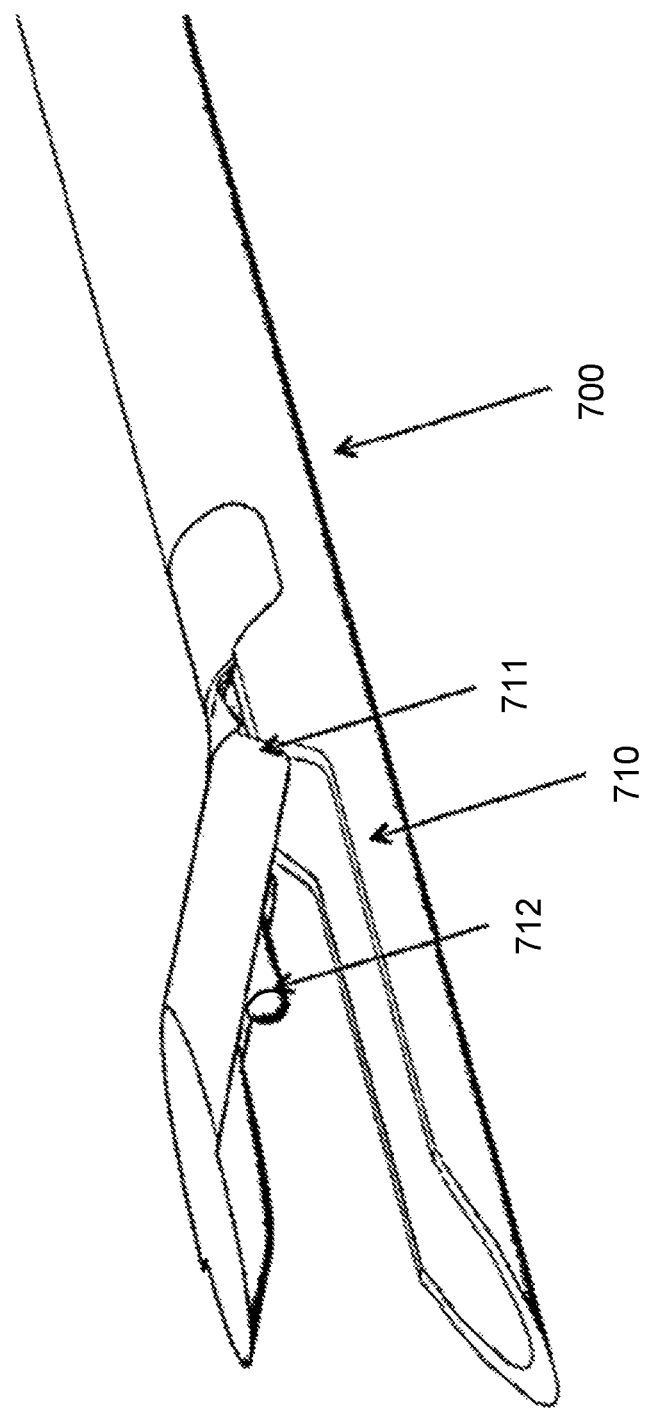

FIG. 7C shows the device 700 with a leaflet separated and camera 712 can be seen in a position where the field of view is looking forward at the field of interest.

FIG. 7D shows the device 700 from a frontal point of view and as with the previous described devices the lumen 790 is unobstructed and fully available for the insertion of tools, fluids or performing aspiration.

Figure 8A:
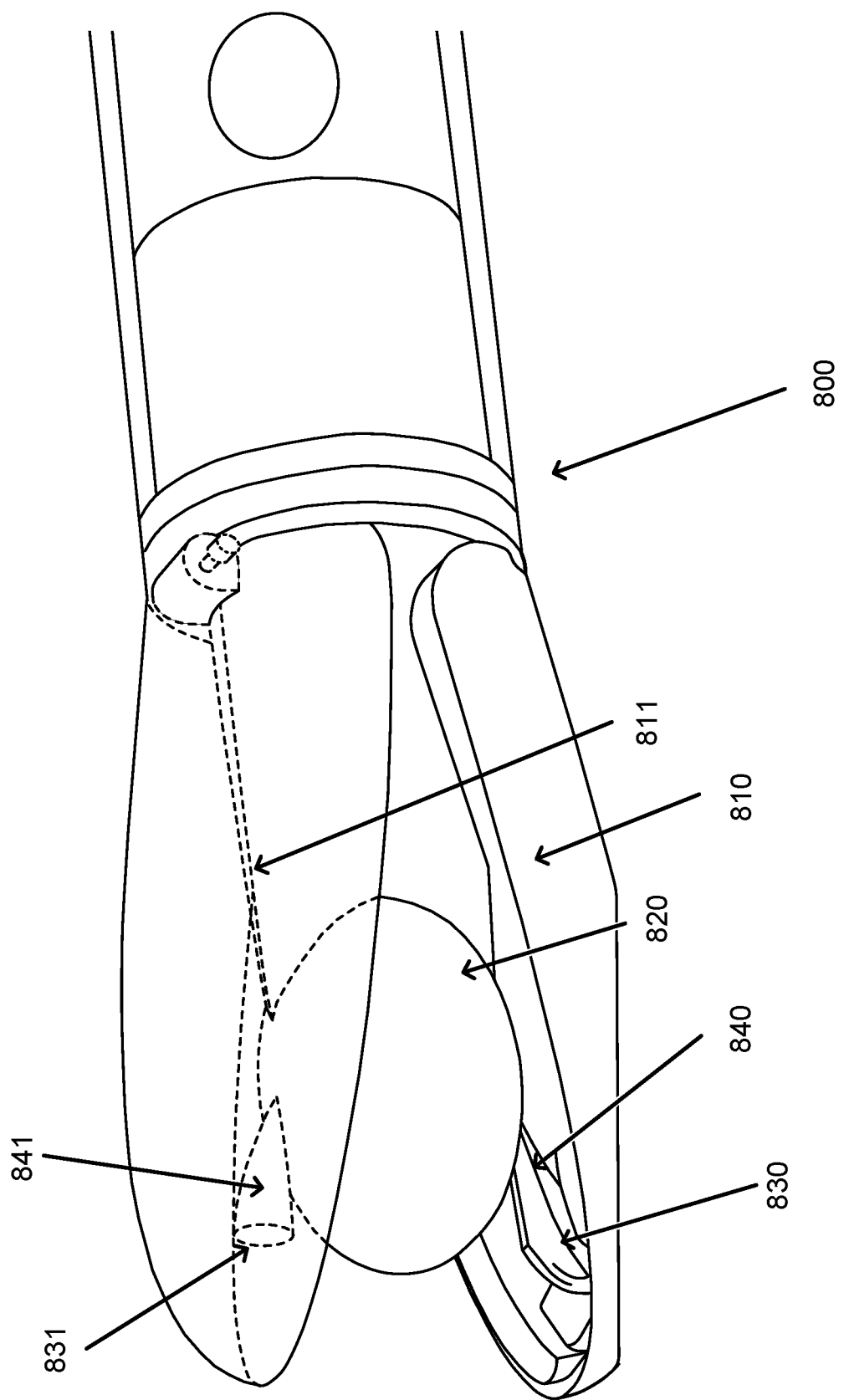
FIGS. 8A-8B show another embodiment where the removal of the resected tissue segment is assisted by the use of high pressure fluid carried to a region near the distal end of the device.
Figure 8B:
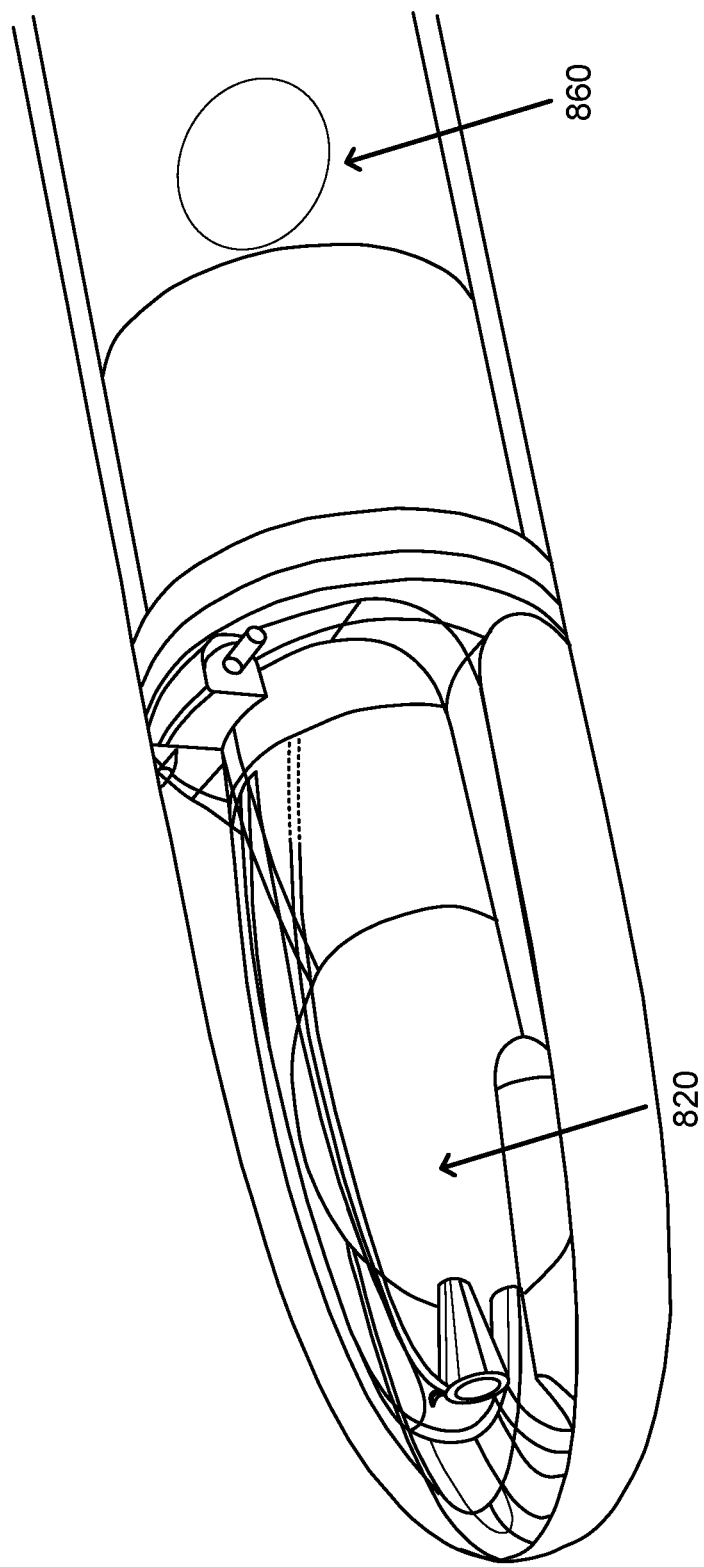

FIG. 8A shows yet another embodiment of the present invention 800 where the removal of the resected tissue segment 820 is assisted by the use of high pressure fluid in two streams of 840 and 841 that are carried to a region near the distal end of the device and once the leaflet 810 and 811 come together and form a seal as in FIG. 8B they induce pressure where they push the resected tissue segment 820 back into the tube 860 and pushes it all the way out of this tube into the proximal section of the tube outside the body of the patient.

Figure 9:
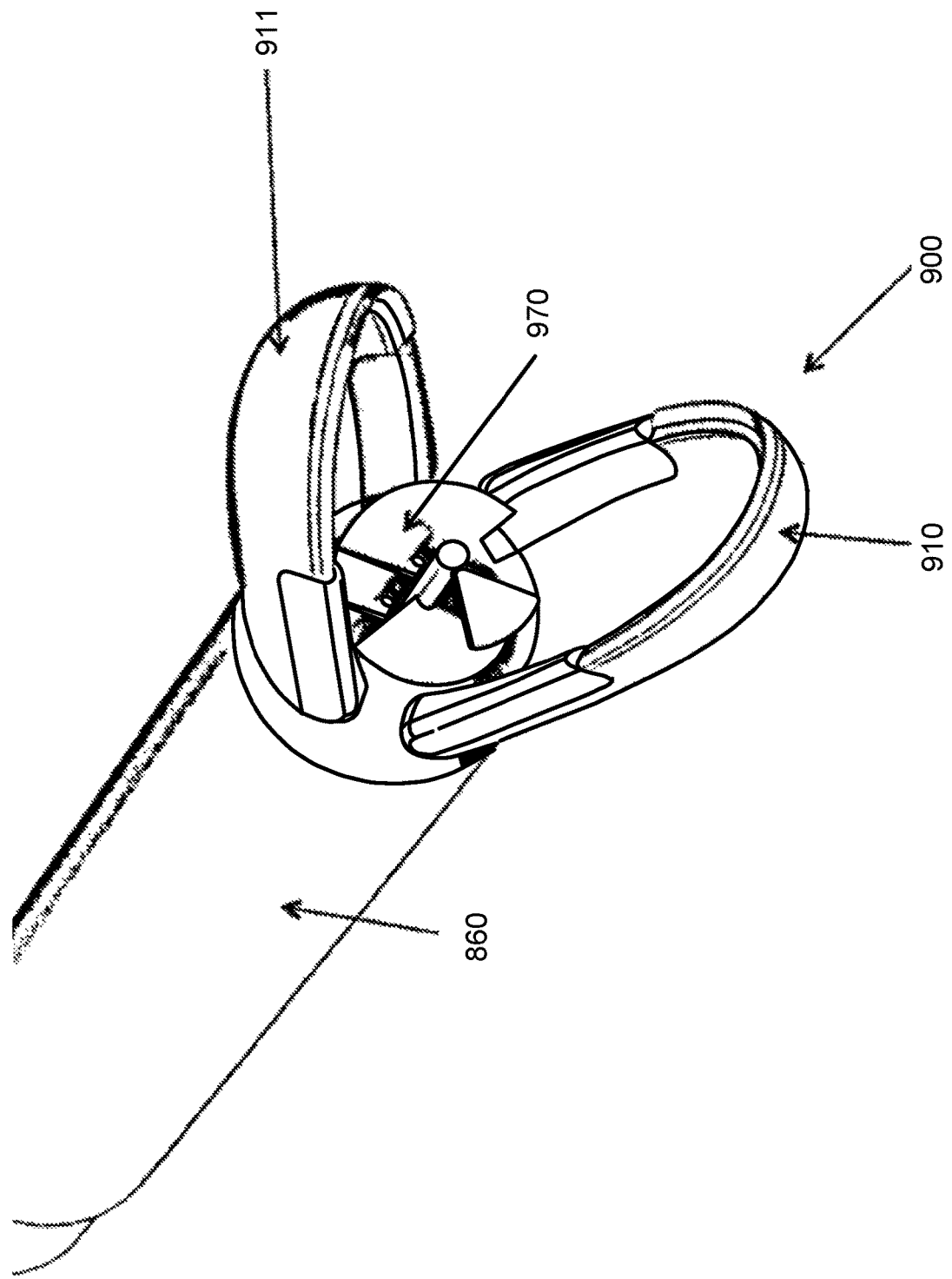
FIG. 9 shows another embodiment where a morcellator assists in the removal of the tissue by breaking it up into small pieces.

FIG. 9 shows another embodiment of this invention where morcellator 970 assists in the removal of the tissue by breaking it up into small pieces and thereby allowing it to be removed by vacuum applied at the proximal end of the tube 960 and prevents the clogging of the tube by a large piece of tissue.

Figure 10:
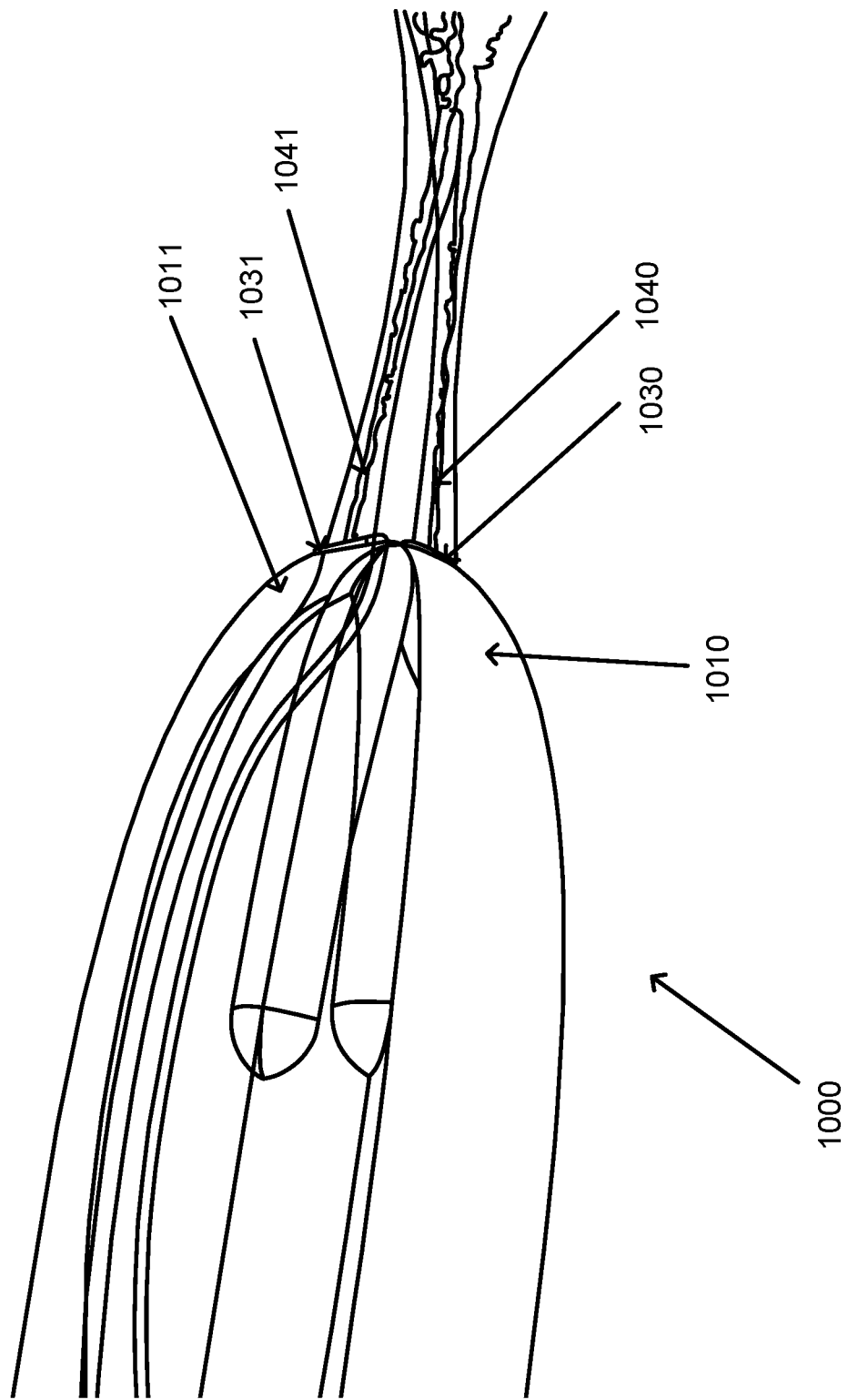
FIG. 10 shows another embodiment whereby two jets of high pressure fluid exit a region near the tip of the device through ports.

FIG. 10 shows another embodiment of the present invention whereby two jets of high pressure fluid 1040 and 1041 exit a region near the tip of the device through ports 1030 and 1031 which are unitary with leaflets 1010 and 1011. Fluid jet 1040 and 1041 exit ports 1030 and 1031 at high velocities enabling the device to perform hydro dissection as known in the art. These jets of fluid can be applied in either open or closed positions of the leaflets.

What is claimed is:

1. A surgical device comprising:
an elongate structure comprising a distal end, a proximal end, a central lumen, and at least one additional lumen;
an expandable space-creating structure mounted in the vicinity of the distal end and configured for placement within a mammalian body proximate to a therapeutic target, wherein the expandable space-creating structure comprises a first leaflet and a second leaflet; and
a proximal terminal comprising an actuator mounted in the vicinity of the proximal end and configured to remain outside of said body and actuate the space-creating structure to cause one or more of the first leaflet or the second leaflet to pivot relative to the elongate structure between a closed configuration and an opened configuration,
wherein the at least one additional lumen includes a first additional lumen configured to carry fluid to and through a first opening in the first leaflet proximate to a tip of the expandable space-creating structure, the first opening facing the second leaflet and configured to direct the fluid toward a space between the first leaflet and the second leaflet, so that, when a resected tissue segment occupies the space between the first leaflet and the second leaflet, the fluid exiting the first opening pushes the resected tissue segment through the elongate structure, towards the proximal terminal, and outside of the mammalian body, and
wherein the at least one additional lumen further includes a second additional lumen configured to carry additional fluid to and through a second opening in the second leaflet proximate to the tip of the expandable space-creating structure, the second opening configured to direct the fluid toward the space between the first leaflet and the second leaflet.

2. The surgical device of claim 1, wherein actuation of the space-creating structure causes only the first leaflet to pivot relative to the elongate structure between the closed configuration and the opened configuration.

3. The surgical device of claim 1, wherein actuation of the space-creating structure causes both the first leaflet and the second leaflet to pivot relative to the elongate structure between the closed configuration and the opened configuration.

4. A surgical device comprising:
an elongate structure comprising a distal end, a proximal end, a central lumen, and at least one additional lumen;
an expandable space-creating structure mounted in the vicinity of the distal end and configured for placement within a mammalian body proximate to a therapeutic target, wherein the expandable space-creating structure comprises a first leaflet and a second leaflet;
a proximal terminal comprising an actuator mounted in the vicinity of the proximal end and configured to remain outside of said body and actuate the space-creating structure to cause one or more of the first leaflet or the second leaflet to pivot relative to the elongate structure between a closed configuration and an opened configuration,
wherein the at least one additional lumen includes a first additional lumen configured to carry fluid to and through a first opening in the first leaflet proximate to a tip of the expandable space-creating structure, the first opening facing the second leaflet and configured to direct the fluid toward a space between the first leaflet and the second leaflet, so that, when a resected tissue segment occupies the space between the first leaflet and the second leaflet, the fluid exiting the first opening pushes the resected tissue segment through the elongate structure, towards the proximal terminal, and outside of the mammalian body; and
a mechanical morcellator mounted in the vicinity of the distal end, wherein the mechanical morcellator is configured for morcellation of the resected tissue segment while the expandable space-creating structure is within the mammalian body.

5. The surgical device of claim 4, wherein the mechanical morcellator is positioned within the central lumen.

6. The surgical device of claim 5, wherein the mechanical morcellator is mounted within an internal space of the expandable space-creating structure.

7. The surgical device of claim 4, further comprising:
a vacuum configured for application at the proximal end of the elongate structure and removal of the morcellated resected tissue segment through the elongate structure.

8. The surgical device of claim 4, wherein actuation of the space-creating structure causes only the first leaflet to pivot relative to the elongate structure between the closed configuration and the opened configuration.

9. The surgical device of claim 4, wherein actuation of the space-creating structure causes both the first leaflet and the second leaflet to pivot relative to the elongate structure between the closed configuration and the opened configuration.

10. A surgical device comprising:
an elongate structure comprising a distal end, a proximal end, a central lumen, and at least one additional lumen;
an expandable space-creating structure mounted in the vicinity of the distal end and configured for placement within a mammalian body proximate to a therapeutic target, wherein the expandable space-creating structure comprises a first leaflet and a second leaflet;
a proximal terminal comprising an actuator mounted in the vicinity of the proximal end and configured to remain outside of said body and actuate the space-creating structure to cause one or more of the first leaflet or the second leaflet to pivot relative to the elongate structure between a closed configuration and an opened configuration,
wherein the at least one additional lumen includes a first additional lumen configured to carry fluid to and through a first opening in the first leaflet proximate to a tip of the expandable space-creating structure, the first opening facing the second leaflet and configured to direct the fluid toward a space between the first leaflet and the second leaflet, so that, when a resected tissue segment occupies the space between the first leaflet and the second leaflet, the fluid exiting the first opening pushes the resected tissue segment through the elongate structure, towards the proximal terminal, and outside of the mammalian body; and
an imaging device comprising an optical axis, wherein the optical axis is configured to extend through the first leaflet in the closed configuration.

11. The surgical device of claim 10, wherein the imaging device is pivotably attached to the first leaflet,
wherein transitioning between the closed configuration and the opened configuration causes the imaging device to pivot so that the optical axis does not extend through the first leaflet, and
wherein the optical axis is substantially parallel to a longitudinal axis of the elongate structure in the closed configuration and wherein transitioning between the closed configuration and the opened configuration causes the optical axis to cross the longitudinal axis.

12. The surgical device of claim 10, wherein one or more of the first leaflet or the second leaflet is optically transparent.

13. The surgical device of claim 10, wherein actuation of the space-creating structure causes only the first leaflet to pivot relative to the elongate structure between the closed configuration and the opened configuration.

14. The surgical device of claim 10, wherein actuation of the space-creating structure causes both the first leaflet and the second leaflet to pivot relative to the elongate structure between the closed configuration and the opened configuration.

15. A surgical device comprising:
an elongate structure comprising a distal end, a proximal end, a central lumen, and at least one additional lumen;
an expandable space-creating structure mounted in the vicinity of the distal end and configured for placement within a mammalian body proximate to a therapeutic target, wherein the expandable space-creating structure comprises a first leaflet and a second leaflet; and
a proximal terminal comprising an actuator mounted in the vicinity of the proximal end and configured to remain outside of said body and actuate the space-creating structure to cause one or more of the first leaflet or the second leaflet to pivot relative to the elongate structure between a closed configuration and an opened configuration,
wherein the at least one additional lumen includes a first additional lumen configured to carry fluid to and through a first opening in the first leaflet proximate to a tip of the expandable space-creating structure, the first opening facing the second leaflet and configured to direct the fluid toward a space between the first leaflet and the second leaflet, so that, when a resected tissue segment occupies the space between the first leaflet and the second leaflet, the fluid exiting the first opening pushes the resected tissue segment through the elongate structure, towards the proximal terminal, and outside of the mammalian body, and
wherein the first leaflet comprises a first electrode and the second leaflet comprises a second electrode, and wherein the first and second electrodes are configured to connect to an energy source and cut or cauterize tissue of the therapeutic target.

16. The surgical device of claim 15, wherein actuation of the space-creating structure causes only the first leaflet to pivot relative to the elongate structure between the closed configuration and the opened configuration.

17. The surgical device of claim 15, wherein actuation of the space-creating structure causes both the first leaflet and the second leaflet to pivot relative to the elongate structure between the closed configuration and the opened configuration.

18. A surgical device, comprising:
an elongate structure comprising a distal end, a proximal end, a central lumen, and at least one additional lumen;
an expandable space-creating structure mounted in the vicinity of the distal end and configured for placement within a mammalian body proximate to a therapeutic target, wherein the expandable space-creating structure comprises a first leaflet and a second leaflet; and
a proximal terminal comprising an actuator mounted in the vicinity of the proximal end and configured to remain outside of said body and actuate the space-creating structure to cause one or more of the first leaflet or the second leaflet to pivot relative to the elongate structure between a closed configuration and an opened configuration,
wherein the at least one additional lumen includes a first additional lumen configured to carry fluid to and through a first opening in the first leaflet proximate to a tip of the expandable space-creating structure, the first opening facing the second leaflet and configured to direct the fluid toward a space between the first leaflet and the second leaflet, so that, when a resected tissue segment occupies the space between the first leaflet and the second leaflet, the fluid exiting the first opening pushes the resected tissue segment through the elongate structure, towards the proximal terminal, and outside of the mammalian body, and
wherein the at least one additional lumen further includes a second additional lumen configured to carry fluid from a second opening in the second leaflet proximate to the tip of the expandable space-creating structure, the fluid exiting the first opening pushing the resected tissue segment via the second opening towards the proximal terminal and outside of the mammalian body.

19. The surgical device of claim 18, wherein actuation of the space-creating structure causes only the first leaflet to pivot relative to the elongate structure between the closed configuration and the opened configuration.

20. The surgical device of claim 18, wherein actuation of the space-creating structure causes both the first leaflet and the second leaflet to pivot relative to the elongate structure between the closed configuration and the opened configuration.

* * * * *